United States Patent
Griffiths et al.

(10) Patent No.: US 11,899,020 B2
(45) Date of Patent: Feb. 13, 2024

(54) SHOTGUN PROTEOMIC ANTIGEN IDENTIFICATION

(71) Applicant: The Regents of the University of California, Oakland, CA (US)

(72) Inventors: Leigh G. Griffiths, Davis, CA (US); Katherine Y. Gates, Davis, CA (US); Ailsa J. Dalgliesh, Davis, CA (US); Maelene L. Wong, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 223 days.

(21) Appl. No.: 16/499,057

(22) PCT Filed: Mar. 29, 2018

(86) PCT No.: PCT/US2018/025251
§ 371 (c)(1),
(2) Date: Sep. 27, 2019

(87) PCT Pub. No.: WO2018/183747
PCT Pub. Date: Oct. 4, 2018

(65) Prior Publication Data
US 2021/0109106 A1 Apr. 15, 2021

Related U.S. Application Data

(60) Provisional application No. 62/479,315, filed on Mar. 31, 2017.

(51) Int. Cl.
*G01N 33/68* (2006.01)
*G01N 33/543* (2006.01)

(52) U.S. Cl.
CPC ... *G01N 33/6842* (2013.01); *G01N 33/54306* (2013.01); *G01N 33/6848* (2013.01); *G01N 33/6857* (2013.01)

(58) Field of Classification Search
CPC ..................................................... G01N 33/68
See application file for complete search history.

(56) References Cited

U.S. PATENT DOCUMENTS

| | | | |
|---|---|---|---|
| 9,220,733 B2 * | 12/2015 | Griffiths | A61L 27/3687 |
| 10,709,813 B2 | 7/2020 | Griffiths et al. | |
| 2004/0101830 A1 | 5/2004 | Hammond et al. | |
| 2006/0270062 A1 | 11/2006 | Nelson et al. | |
| 2007/0178541 A1 * | 8/2007 | Pedersen | G01N 33/564 |
| | | | 435/7.32 |
| 2008/0039338 A1 | 2/2008 | Buechler et al. | |
| 2013/0243738 A1 | 9/2013 | Griffiths et al. | |
| 2016/0184478 A1 | 6/2016 | Griffiths et al. | |
| 2020/0390935 A1 | 12/2020 | Griffiths et al. | |

FOREIGN PATENT DOCUMENTS

| | | |
|---|---|---|
| WO | WO-2004/007717 A1 | 1/2004 |
| WO | WO-2011/132089 A2 | 10/2011 |
| WO | WO-2012/012693 A2 | 1/2012 |
| WO | WO-2014/077934 A1 | 5/2014 |

OTHER PUBLICATIONS

Mahmood et al., Western Blot: Technique, Theory, and Trouble Shooting, North American Journal of Medical Sciences, 2012, 4(9), 429-434. (Year: 2012).*
Sakamoto et al., Enzyme-Linked Immunosorbent Assay for the Quantitative/Qualitative Analysis of Plant Secondary Metabolites, Journal of Natural Medicines, 2018, 72, 32-42. (Year: 2018).*
International Search Report and Written Opinion dated Jun. 15, 2018, from application No. PCT/US2018/025251.
Badylak, et al., "Extracellular matrix as a biological scaffold material: Structure and function", Acta Biomater. (Jan. 2009) 5(1):1-13, doi:10.1016/j.actbio.2008.09.013.
Baker, et al., "Mass spectrometry for translational proteomics: progress and clinical implications", Genome Med. (Aug. 2012) 4(8):63. doi:10.1186/gm364.
Cordwell, SJ, "Sequential extraction of proteins by chemical reagents", Methods Mol. Biol. (2008) 424:139-146.
Dong, et al., "RGD-modified acellular bovine pericardium as a bioprosthetic scaffold for tissue engineering", J Mater Sci Mater Med. (Nov. 2009) 20(11):2327-36. doi:10.1007/s10856-009-3791-4.
Fitzgerald, et.al, "Immunoaffinity chromatography", Methods Mol Biol. (2011) 681:35-59.
Fitzgerald, et.al., "Immunoaffinity Chromatography: Concepts and Applications", Methods Mol Biol. (2017) 1485:27-51.
Gershon, "Cleaved and missed sites for trypsin, lys-C, and lys-N can be predicted with high confidence on the basis of sequence context", J Proteome Res. (Feb. 7, 2014) 13(2):702-9.
Gilles, et al. (2011) "Method for Decellularizing Skeletal Muscle Without Detergents or Proteolytic Enzymes" Tissue Engineering: Part C, 17(4): 383-389.
Griffiths et al., "Immunoproteomic identification of bovine pericardium xenoantigens", Biomaterials, 2008, vol. 29, pp. 3514-3520.
Griffiths, et al., "Protein extraction and 2-de of water- and lipid-soluble proteins from bovine pericardium, a low-cellularity tissue", Electrophoresis. (2008) 29:4508-4515.
Kabat, et al., "Identical V region amino acid sequences and segments of sequences in antibodies of different specificities. Relative contributions of VH and VL genes, minigenes, and complementarity-determining regions to binding of antibody-combining sites", J Immunol. (Sep. 1991) 147(5):1709-19.
Kasimir, et al., "Decellularization does not eliminate thrombogenicity and inflammatory stimulation in tissue-engineered porcine heart valves", J Heart Valve Dis. (Mar. 2006) 15(2):278-86; discussion 286.
Kasimir, et al., "Presence and elimination of the xenoantigen gal (alpha1, 3) gal in tissue-engineered heart valves", Tissue Eng. (2005) 11:1274-1280.

(Continued)

*Primary Examiner* — Amy M Bunker
(74) *Attorney, Agent, or Firm* — Foley & Lardner LLP

(57) ABSTRACT

This invention provides methods for the screening and identification of antigenic components in a tissue or organ of interest.

11 Claims, 7 Drawing Sheets

(56) References Cited

OTHER PUBLICATIONS

Kasmir, et al., "Comparison of different decellularization procedures of porcine heart valves", Int. J. Artif. Organs. (2003) 26:421-427.
Lehner, et al., "An optimized method for the isolation and identification of membrane proteins", Electrophoresis. (2003) 24: 1795-1808.
Leimgruber, et al., "Development of improved cell lysis, solubilization and imaging approaches for proteomic analyses", Proteomics. (2002) 2:135-144.
Li, et al., "Evaluation of several two-dimensional gel electrophoresis techniques in cardiac proteomics", Electrophoresis. (Sep. 2005) 26(18):3572-85. doi:10.1002/elps.200500104.
Magdeldin, et al., "Basics and recent advances of two dimensional-polyacrylamide gel electrophoresis", Clin Proteomics. (Apr. 2014) 11(1):16. doi:10.1186/1559-0275-11-16.
Manji, et al., "Glutaraldehyde-fixed bioprosthetic heart valve conduits calcify and fail from xenograft rejection", Circulation (Jul. 2006) 114(4):318-327, doi:10.1161/CIRCULATIONAHA.105.549311.
Manji, et al., "Xenograft bioprosthetic heart valves: Past, present and future", Int J Surg. (Nov. 2015) 23(Pt B):280-284. doi:10.1016/j.ijsu.2015.07.009.
Molloy, et al., "Extraction of membrane proteins by differential solubilization for separation using two-dimensional gel electrophoresis", Electrophoresis. (1998) 19:837-844.
Non-Final Office Action on U.S. Appl. No. 16/912,586 dated Jul. 8, 2022 (10 pages).
Nozaki, et al., "The solubility of amino acids and related compounds in aqueous urea solutions", J. Biol. Chem. (1963) 238:4074-4081.
Nozaki, et al., "The solubility of amino acids and two glycine peptides in aqueous ethanol and dioxane solutions", J. Biol. Chem. (1971) 246:2211-2217.
Papalamprou (2013) "Antigen Removal for the Production of Immunoacceptable Xenogenic Scaffolds for Myocardial Patch Tissue Engineering" presented to Molecular, Cellular & Integrative Physiology (MCIP) Colloquium at University of California, Davis on Mar. 1, 2013, 17 Pages.
Papalamprou, et al. (2013) "Antigen Removal for the Production of Immunoacceptable Xenogenic Scaffolds for Myocardial Patch Tissue Engineering" Biomedical Engineering Society, 2013 annual meeting: Sep. 25-28, 2013, 1 Page [Abstract].
Posch, et al., "2D-ToGo workflow: increasing feasibility and reproducibility of 2-dimensional gel electrophoresis", Arch Physiol Biochem. (Jul. 2013) 119(3):108-13. doi:10.3109/13813455.2013.791699.
Rabilloud, T., "Membrane proteins and proteomics: love is possible, but so difficult", Electrophoresis. (Jun. 2009) 30 Suppl 1:S174-80. doi:10.1002/elps.200900050.
Sisson, et al., "An improved method for immobilizing IgG antibodies on protein A-agarose", J. Immunol. Methods (Mar. 1990.) 127(2):215-220.
Thermo Fisher (https://tools.thermofisher.com/content/sfs/brochures/TR0005-Attach-Ab-glass.pdf.
UniProt, C., "UniProt: a hub for protein information", Nucleic Acids Res. (Jan. 2015) 43(Database issue):D204-12.doi:10.1093/nar/gku989.
Wheeler, et al., "Characterization of endothelial antigens associated with transplant-associated coronary artery disease", J Heart Lung Transplant. (Nov.-Dec. 1995) 14(6 Pt 2):S188-97.
Wong, et al. (2010) "Maintained Protein Solubility Enhances Antigen Removal from Xenogeneic Tissue for Heart Valve Tissue Engineering" Tissue Engineering and Regenerative Medicine, International Society, 2010 North America annual meeting: Dec. 5-8, 2010,One Page [Abstract].
Wong, et al. (2010) "Protein Solubilization for Antigen Removal from Bovine Pericardium in Heart Valve Tissue Engineering" Biomedical Engineering Society, 2010 annual meeting: Oct. 6-9, 2010, One Page [Abstract].
Wong, et al. (2011) "Antigen Removal Does Not Compromise Xenograft Properties or Correlate to Histological Acellularity" Biomedical Engineering Society, 2011 annual meeting: Oct. 12-15, 2011, One Page [Abstract].
Wong, et al. (2011) "Effect of Chaotropes on Antigen Removal in Xenogeneic Scaffold Generation" Tissue Engineering and Regenerative Medicine, International Society, 2011 North America annual meeting: Dec. 11-14, 2011, One Page [Abstract].
Wong, et al. (2011) "Sequential, Differential Solubilization for Antigen Removal in Xenogeneic Scaffold Generation" Tissue Engineering and Regenerative Medicine, International Society, 2011 North America annual meeting: Dec. 11-14, 2011, One Page [Abstract].
Wong, et al. (2012) "Stepwise, Solubilization-Based Antigen Removal Maintains Xenogeneic Scaffold Properties" Biomedical Engineering Society, 2012 annual meeting: Oct. 24-27, 2012, One Page [Abstract].
Wong, et al. (2013) "Effect of stepwise, solubilization-based antigen removal on in vivo immune response to xenogeneic scaffolds" Cellular and Molecular Bioengineering 2013 Annual Conference: Jan. 2-5, 2013, One Page [Abstract].
Wong, et al. (2013) "Stepwise, Solubilization-Based Antigen Removal Maintains Xenogeneic Scaffold Recellularization Capacity" Biomedical Engineering Society, 2013 annual meeting: Sep. 25-28, 2013, One Page [Abstract].
Wong, et al., "Immunogenicity in xenogeneic scaffold generation: Antigen removal vs. decellularization" (2014) Acta Biomaterialia 10: 1806-1816.
Wong, et al., "Stepwise solubilization-based antigen removal for xenogeneic scaffold generation in tissue engineering", Acta Biomater (May 2013) 9(5)6492-501, doi: 10.1016/j.actbio.2012.12.034.
Wong, et al., "The role of protein solubilization in antigen removal from xenogeneic tissue for heart valve tissue engineering", Biomaterials, 2011, vol. 32, pp. 8129-8138.
Wu, et al., "Possible use of similar framework region amino acid sequences between human and mouse immunoglobulins for humanizing mouse antibodies", Mol Immunol. (Sep. 1992.) 29(9):1141-6.
Zhang, et al, "A novel antibody immobilization and its application in immunoaffinity chromatography", Talanta (Jul. 2010) 82(2):704-709.
Zilla, et al., "Bioprosthetic heart valves: the need for a quantum leap", Biotechnol Appl Biochem. (Aug. 2004) 40(Pt 1):57-66. doi:10.1042/Ba20030211.
U.S. Appl. No. 18/105,205, filed Feb. 2, 2023, Leigh G. Griffiths et al.
Amended Claims as filed in U.S. Appl. No. 18/105,205 on Sep. 26, 2023 in response to Notice to File Missing Parts, 6 pages.
Notice to File Missing Parts of Non-Provisional Application in U.S. Appl. No. 18/105,205 dated Mar. 8, 2023, 2 pages.

* cited by examiner

Fig. 2A-C

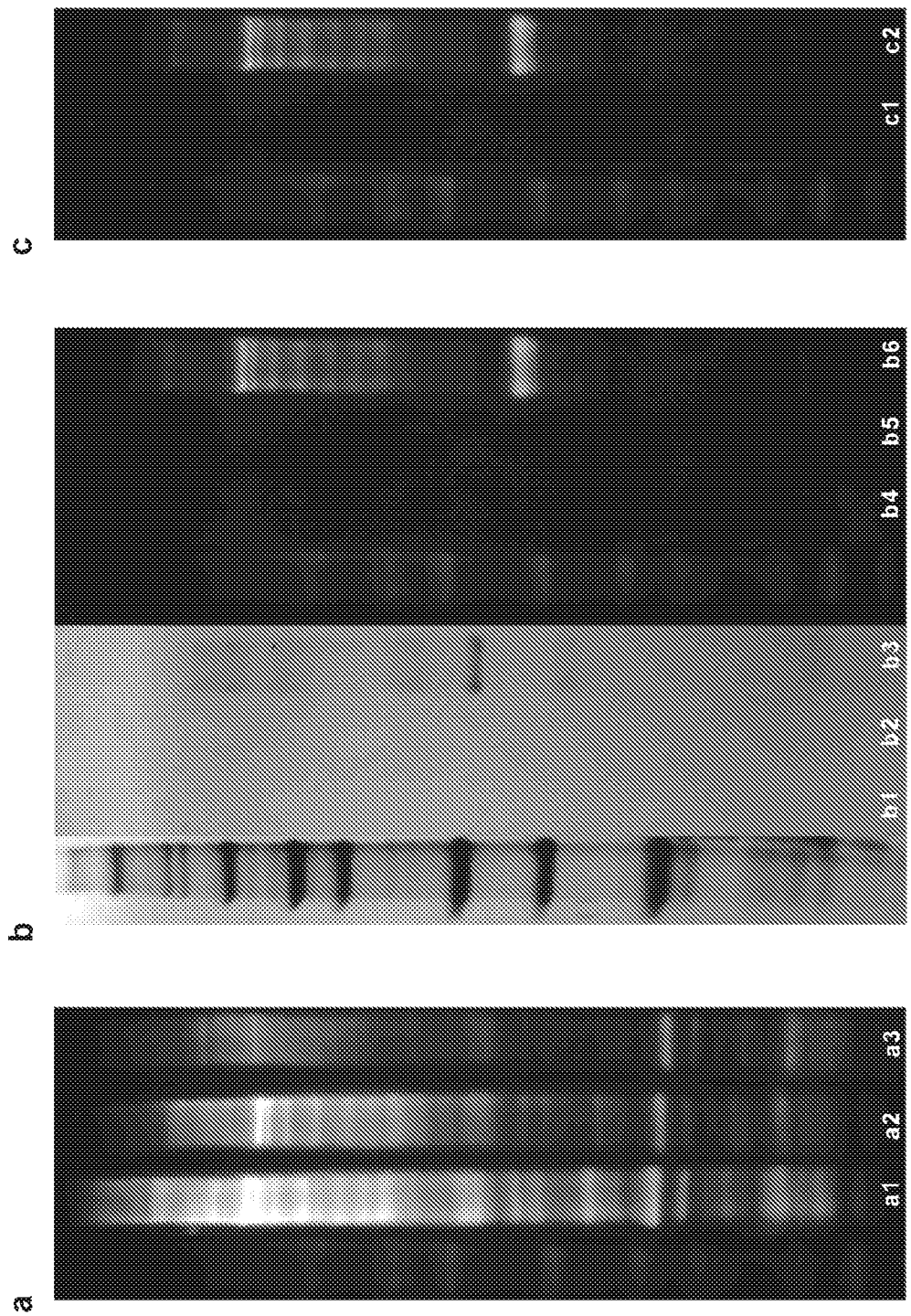
Fig. 4A-C a
b
*Fig. 5A-C*

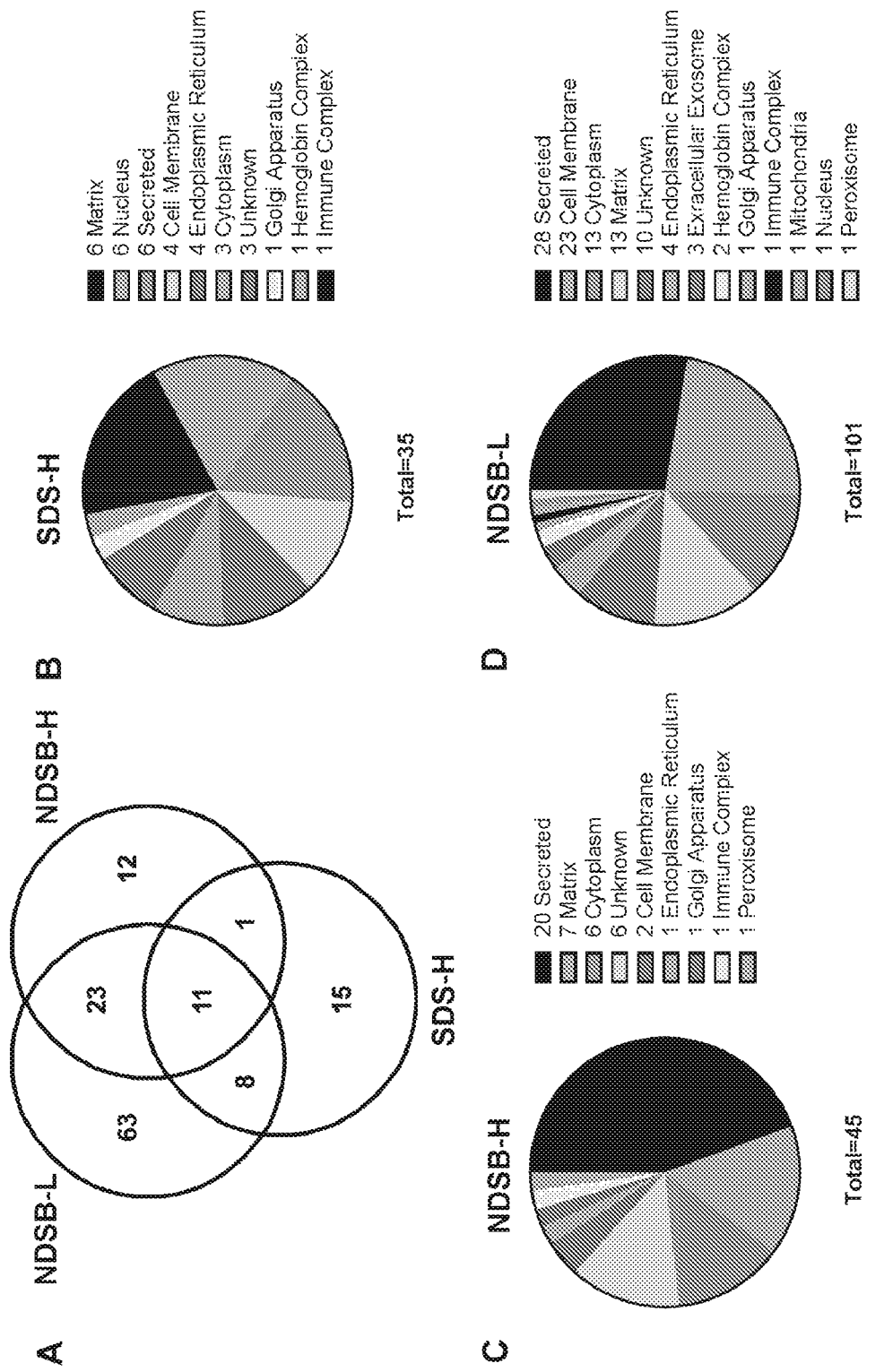
Fig. 6A-D

SHOTGUN PROTEOMIC ANTIGEN IDENTIFICATION

CROSS-REFERENCE TO RELATED APPLICATIONS

This application is a national stage application under 35 U.S.C. § 371 of International Application No. PCT/US2018/025251, filed Mar. 29, 2018, which claims the benefit under 35 U.S.C. 119(e) of U.S. Provisional Application No. 62/479,315, filed on Mar. 31, 2017, the contents of each of which are hereby incorporated by reference in their entireties for all purposes.

STATEMENT OF GOVERNMENTAL SUPPORT

This work was supported in part by Grant Nos. R01HL115205 and 5T32OD010931-10 from the National Institutes of Health. The Government has certain rights in this invention.

BACKGROUND

Biomaterial antigenicity represents the primary barrier to expanding the use of xenogeneic biomaterials in clinical practice (1). Although fixed and unfixed xenogeneic biomaterials are commonly used in clinical practice, recipient graft-specific immune responses limit their long term durability and functional outcomes (2,3). Clinical results achieved with such biomaterials are far from ideal, with both acute rejection (i.e., decellularized) (4) and chronic rejection (i.e., glutaraldehyde-fixation) responses being reported (5). Bovine pericardium (BP) has a native extracellular matrix (ECM) architecture that encompasses apposite structure/function properties and an essential ECM niche environment ideal for cell migration and proliferation (6). However, ameliorating xenogeneic tissue antigenicity prior to implantation is critical in avoiding recipient graft-specific in vivo immune responses (7). In an attempt to produce immunologically-acceptable xenogeneic tissue ECM scaffolds for clinical application, decellularization approaches have largely focused on ECM scaffold cellularity as the primary predictor of recipient graft-specific response (6,8). However, scaffold cellularity is a poor predictor of in vivo recipient graft-specific immune response and insufficient removal of antigens in decellularized tissue has potential to result in a catastrophic graft-specific immune response (9). Recent studies have demonstrated that specific assessment and removal of ECM scaffold antigens prior to in vivo implantation more strongly correlates with reduced recipient graft-specific adaptive immune responses (10). Future progress in the field of xenogeneic tissue scaffolds is therefore reliant on increased understanding of the antigenicity of such biomaterials, driving the need for high-throughput methods of antigen identification. In identifying the determinants of xenoantigenicity, we can improve our understanding and monitoring of immune responses toward clinically utilized biomaterials and inform efforts designed to reduce antigenicity of next generation xenogeneic biomaterials.

Immunoproteomic identification of antigenic determinants of xenogeneic biomaterials has previously relied on the use of two-dimensional (2-DE) Western blots, which are time consuming, and suffer from challenging reproducibility and limited capacity for separation of highly lipophilic proteins (11,12). The process of creating large-format 2-DE gels, running associated Western blots, isolating antigenic protein spots, and submitting samples for further proteomic analysis can take weeks for each positive protein identification (13). Additionally, the commonly utilized practice of in-silico comparison between Western blots and duplicate gels introduces a potential source of error in ultimate identifications, particularly when considering the challenging reproducibility of 2-DE based approaches (14). Furthermore, the limited dynamic range, particularly of silver stained gels, further reduces the accuracy of antigen quantification (14). Finally, the challenges inherent in maintaining protein solubility during isoelectric focusing (IEF) limit the ability of 2-DE approaches to resolve highly lipophilic membrane proteins (12).

SUMMARY

In one aspect, provided are methods for screening and identification of antigenic components of a tissue and/or an organ or an infectious agent or organism. In some embodiments, the methods comprise the steps of:
 a) obtaining a biological sample from a subject who has been exposed to antigenic components of the tissue and/or the organ or infectious agent or organism;
 b) attaching immunoglobulins, or fragments thereof, from the biological sample to a stationary or solid support, thereby creating a stationary or solid phase comprising immobilized immunoglobulins, or fragments thereof;
 c) extracting hydrophilic and/or lipophilic components from the tissue and/or the organ or infectious agent or organism;
 d) exposing the extracted components to the stationary or solid phase comprising immobilized immunoglobulins, or fragments thereof, under conditions that allow antigenic components to bind to the immunoglobulins, or fragments thereof;
 e) washing the stationary or solid phase to remove unbound components;
 f) eluting bound antigenic components from the immobilized immunoglobulins, or fragments thereof; and
 g) identifying the bound and then eluted antigenic components by mass spectrometry. In varying embodiments, the biological sample comprises serum or plasma. In varying embodiments, the tissue and/or organ is transplant tissue and/or organ. In varying embodiments, the transplant tissue and/or organ is syngeneic, allogeneic or xenogeneic. In varying embodiments, the tissue and/or organ is cancerous or infected with the infectious agent or organism. In varying embodiments, the tissue and/or organ is targeted in an autoimmune disease or secondary to an infectious disease. In varying embodiments, the infectious agent or organism is bacterial or viral. In varying embodiments, the subject is a human. In varying embodiments, the subject is a non-human mammal. In varying embodiments, the subject has been immunized with a sample of the tissue and/or the organ. In varying embodiments, the sample of tissue or organ has been homogenized. In varying embodiments, the stationary or solid phase binds to the Fc portion of the immunoglobulins. In varying embodiments, the immunoglobulins are covalently bound to the stationary or solid phase. In varying embodiments, the stationary or solid phase is packed in a column. In varying embodiments, the immunoglobulins are whole immunoglobulin molecules. In varying embodiments, the immunoglobulins are fragments, such as Fv, scFv, dsFv, Fab, Fab', F(ab')$_2$. In varying embodiments, the immunoglobulins comprise nanobodies, e.g., camelid VHH. In varying embodiments, the immunoglobulins are an immunoglobulin subclass selected from the group consisting of IgG, IgM, IgE, IgA, IgD, and mixtures thereof. In varying embodiments, the immunoglobulins are IgG subclass immunoglobulins. In varying embodiments, the immunoglobulins comprise IgG subclass immunoglobulins selected from the group IgG1, IgG2, IgG3, IgG4, and mixtures thereof. In varying embodiments, the immunoglobulins are concentrated, isolated and/or purified prior to attachment to the stationary or solid phase. In varying embodiments, the antigenic components comprise proteins, carbohydrates and/or lipids. In varying embodiments, hydrophilic antigenic components are extracted. In varying embodiments, the hydrophilic antigenic components are extracted by exposing the tissue or organ to one or more agents selected from the group consisting of a non-detergent sulfobetaine (NDSB) (e.g., NDSB-256, NDSB-201, aminosulfobetaine 14 (ASB-14), aminosulfobetaine 16 (ASB-16), 4-n-Octylbenzoylamido-propyl-dimethyl-ammonio sulfobetaine (ASB-C8Ø), sulfobetaine 3-10, sulfobetaine 3-14, sulfobetaine 3-16, sulfobetaine 3-8, sulfobetaine 3-18), cetyltrimethylammonium bromide (CTAB), C7BzO, 0.1% sodium dodecyl sulfate (SDS), sodium octyl sulfate, Triton X-100, Triton X-114, digitonin, saponin, maltosides (e.g., n-decyl-β-D-maltopyranoside (DM), n dodecyl β-D-maltoside (DDM), 6-Cyclohexyl-1-hexyl-β-D-maltopyranoside (Cymal-6)), Brij 35, Brij 58, IGEPAL CA-630, Nonidet P40, TWEEN 20, TWEEN 40, TWEEN 60, TWEEN 80, bile salts (e.g., cholic acid, lithocholic acid, glycocholic acid, deoxycholic acid, sodium deoxycholate, 3-[(3-cholamidylpropyl)dimethylammonio]-1-propane sulfonate (CHAPS), 3-([3-cholamidopropyl]dimethyl-ammonio)-2-hydroxy-1-propanesulfonate (CHAPSO)), cetyltrimethylammonium bromide (CTAB), urea, and thiourea. In varying embodiments, the lipophilic antigenic components are extracted. In varying embodiments, the lipophilic antigenic components are extracted by exposing the tissue or organ to one or more agents selected from the group consisting of a non-detergent sulfobetaine (NDSB) (e.g., NDSB-256, NDSB-201, aminosulfobetaine 14 (ASB-14), aminosulfobetaine 16 (ASB-16), 4-n-Octylbenzoylamido-propyl-dimethylammonio sulfobetaine (ASB-C8Ø), sulfobetaine 3-10, sulfobetaine 3-14, sulfobetaine 3-16, sulfobetaine 3-8, sulfobetaine 3-18), cetyltrimethylammonium bromide (CTAB), C7BzO, 1.0% sodium dodecyl sulfate (SDS), sodium octyl sulfate, Triton X-100, Triton X-114, digitonin, saponin, maltosides (e.g., n-decyl-β-D-maltopyranoside (DM), n dodecyl β-D-maltoside (DDM), 6-Cyclohexyl-1-hexyl-β-D-maltopyranoside (Cymal-6)), Brij 35, Brij 58, IGEPAL CA-630, Nonidet P40, TWEEN 20, TWEEN 40, TWEEN 60, TWEEN 80, bile salts (e.g., cholic acid, lithocholic acid, glycocholic acid, deoxycholic acid, sodium deoxycholate, 3-[(3-cholamidylpropyl)dimethylammonio]-1-propane sulfonate (CHAPS), 3-([3-cholamidopropyl]dimethylammonio)-2-hydroxy-1-propanesulfonate (CHAPSO)), cetyltrimethylammonium bromide (CTAB), urea, and thiourea, wherein the lipophilic antigenic components are extracted by exposing the tissue or organ to a concentration of agent that is at least about 5-fold, e.g., at least about 6-fold, 7-fold, 8-fold, 9-fold, 10-fold, or more, of the concentration of agent used or necessary to extract hydrophilic antigenic components. In varying embodiments, the lipophilic antigenic components are extracted by exposing the tissue or organ to non-detergent sulfobetaine 256 plus n-dodecyl-β-D-maltoside. In varying embodiments, the lipophilic antigenic components are extracted by exposing the tissue or organ to a cyclodextrin derivative, a high molecular weight pullulan, or mixtures thereof. In varying embodiments, the eluting step comprises step-wise elution. In varying embodiments, the eluting step comprises exposing the bound antigenic components to increasing salt concentration. In varying embodiments, the eluting step comprises exposing the bound antigenic components to increasing acetonitrile concentration. In varying embodiments, the eluting step comprises exposing the bound antigenic components to decreasing pH. In varying embodiments, the eluting step comprises exposing the bound antigenic components to increasing pH. In varying embodiments, the eluted antigenic components are identified by liquid chromatography-mass spectrometry (LC-MS/MS). In varying embodiments, the eluted antigenic components are identified by matrix-assisted laser desorption-ionization (MALDI) or surface-enhanced laser desorption/ionization (SELDI). In varying embodiments, the method is multiplexed. In varying embodiments, at least 2 samples, e.g., at least 4, 6, 8, 10, 12, 14, 16 18, 20, 22, 24, 26, 28 or 30 samples, or more, are run in parallel. In varying embodiments, the method can be completed in 12, 11, 10, 9, 8, 7, 6, 5 or fewer hours.

Definitions

The term "isolated," and variants thereof, denotes that the immunoglobulin or extracted component (e.g., protein, carbohydrate, lipid, nucleic acid) is essentially free of other cellular components with which it is associated in the natural state. It is preferably in a homogeneous state. Purity and homogeneity are typically determined using known techniques, such as polyacrylamide gel electrophoresis or high performance liquid chromatography. A protein that is the predominant species present in a preparation is substantially purified.

The term "purified" denotes that an immunoglobulin or extracted component (e.g., protein, carbohydrate, lipid, nucleic acid) is at least 80%, 85% or 90% pure, more preferably at least 95% pure, and most preferably at least 99% pure.

The term "enriched" refers to an increased concentration compared to the natural state, e.g., at least about 10%, 20%, 30%, 40%, 50%, 60%, 70%, 80%, 90%, 95%, 99%, or more, increased concentration as compared the natural state, e.g., in its original cellular or tissue environment prior to extraction.

An "antibody" refers to a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains, respectively. As used in this application, an "antibody" encompasses all variations of antibody and fragments thereof that possess a particular binding specifically, e.g., for tumor associated antigens. Thus, within the scope of this concept are full length antibodies, chimeric antibodies, humanized antibodies, human antibodies, unibodies, single domain antibodies or nanobodies, single chain antibodies (ScFv), Fab, Fab', and multimeric versions of these fragments (e.g., F(ab')$_2$) with the same binding specificity.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. See, Kabat and Wu, SEQUENCES OF PROTEINS OF IMMUNOLOGICAL INTEREST, U.S. Government Printing Office, NIH Publication No. 91-3242 (1991); Kabat and Wu, J Immunol. (1991) 147(5):1709-19; and Wu and Kabat, *Mol Immunol.* (1992) 29(9):1141-6. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

References to "VH" refer to the variable region of an immunoglobulin heavy chain, including an Fv, scFv, dsFv or Fab. References to "VL" refer to the variable region of an immunoglobulin light chain, including of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The terms "tissue" or "biological tissue" interchangeably refer to a collection of interconnected cells and extracellular matrix that perform a similar function or functions within an organism. Biological tissues include, without limitation, connective tissue, muscle tissue, nervous tissue (of the brain, spinal cord, and nerves), epithelial tissue, and organ tissue. Connective tissue includes fibrous tissue, e.g., fascia, tendon, ligaments, heart valves, bone, and cartilage. Muscle tissue includes skeletal muscle tissue, smooth muscle tissue, e.g., esophageal, stomach, intestinal, bronchial, uterine, urethral, bladder, and blood vessel tissue, and cardiac muscle tissue. Epithelial or endothelial tissue includes simple epithelial tissue, e.g., alveolar epithelial tissue, blood vessel endothelial tissue, and heart mesothelial tissue, and stratified epithelial tissue. The biological tissue can additionally be selected, without limitation, from the group consisting of heart valve, vessel, vascular conduit, artery, vein, skin, dermis, epidermis, pericardium, dura, intestinal submucosa, intestine, ligament, tendon, bone, cartilage, ureter, urinary bladder, liver, lung, thymus, spleen, kidney, umbilical cord, cornea, nerve, brain, pituitary, thyroid, parathyroid, pancreas, adrenal gland, lymph node, and heart. Multiple tissues/tissue types comprise organs. Organs are included herein under the terms "tissue and/or "biological tissue."

The phase "intact tissue" refers to tissue that has not been minced or homogenized. The intact tissue may be a whole tissue or a complete organ.

The term "organ" as used herein refers to a collection of tissues joined in a structural unit to serve a common function.

The term "dermis" as used herein refers to the layer of skin between the epidermis and the subcutaneous tissues.

The term "epithelial tissue" as used herein refers to the tissue covering the whole surface of the body or lining certain organ systems exposed to the external environment, such as the gastrointestinal tract, the urogenital tract, or the lung. It is made up of cells closely packed and arranged in at least one layer. This tissue is specialized to form a covering or lining of all internal and external body surfaces.

The term "endothelial tissue" or "endothelium" as used herein refers to a type of epithelium that lines the cavities of the heart, the interior surface of blood vessels and lymphatic vessels, forming an interface between circulating blood or lymph in the lumen and the rest of the vessel wall. It is a thin layer of simple squamous cells called endothelial cells.

The terms "patient," "subject" or "individual" interchangeably refers to a mammal, for example, a human or a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., *rattus*, murine, lagomorpha, hamster).

The term "cellular and/or soluble macromolecular component" as used herein refers to soluble substances constituting portions of the cell or produced by cells, including cell membranes, cytosol, and soluble macromolecules (e.g. proteins, nucleic acids, polypeptides, glycoproteins, carbohydrates, lipids, phospholipids, etc.). Cellular and/or soluble macromolecular components that induce an immune response in a subject are immunogenic antigens.

The term "sulfobetaine" refers to zwitterionic amphiphilic molecules that contain a polarized sulfobetaine head group (e.g., dimethylsulfonioacetate $(CH_3)_2S^+$—$CH_2$—$CO_2^-$). In various embodiments, the head group is followed by a three-carbon linkage between the quaternary ammonium and the amido nitrogen. In various embodiments, the sulfobetaine comprises a linear hydrocarbon tail composed of 13 to 16 carbons. The sulfobetaine can be a detergent or a non-detergent molecule.

BRIEF DESCRIPTION OF THE DRAWINGS

FIGS. 4A-C illustrate Western blot and silver stain of protein eluates. Western blot of total native protein extract (a1), protein extract run-through from D0 column (a2), and protein extract run-through from D84 column (a3). Both D0 and D84 columns demonstrate decreased antigenic protein content in column run-through, with greater removal of antigenic bands in D84 column. Silver stain for SDS-page gel of D84 pH 5, 4, and 2.9 eluates ((b1,b2 and b3) respectively) and corresponding D84 Western blot from pH 5, 4, and 2.9 eluates ((b4,b5 and b6) respectively), confirming that minimal non-specific binding is present and that all specifically bound proteins (pH 2.9 eluates) are antigenic. Comparison of D0 and D84 eluates at pH 2.9, demonstrating that more antigens are specifically captured from D84 columns (c2) than from D0 columns (c1). (n=4 per extraction method and timepoint). Western blot and silver stained gel were cropped for easier visualization, uncropped images are available in the supplemental material.

FIGS. 5A-B illustrate original Western blot and silver stain for the SDS-page gel containing eluent and eluates of Day 0 and Day 84 SpinTrap columns. Western blot (a) of total native protein extract (a13), protein extract run-through from D0 column (a1), and protein extract run-through from D84 column (a7). Both D0 and D84 columns demonstrate decreased antigenic protein content in column run-through, with greater removal of antigenic bands in D84 column. Silver stain (b) for SDS-page gel of D84 pH 5, 4, and 2.9 eluates (b9, b10, and b11 respectively) and from corresponding D84 Western blot pH 5, 4, and 2.9 eluates (a8, a9, and a11) respectively), confirming that minimal non-specific binding is present and that all specifically bound proteins (pH 2.9 eluates) are antigenic. Comparison of D0 and D84 eluates at pH 2.9, demonstrating that more antigens are specifically captured from D84 columns (a10) than from D0 columns (a6). (n=4).

FIGS. 6A-D illustrate a comparison of antigenic protein identifications depending on type of extraction solution, SDS-H, NDSB-H, and NDSB-L. Venn diagram showing the number of antigenic proteins identified using each protein extraction methods (a). Pie charts demonstrating subcellular location of proteins depending on the protein extraction method used (b-d). Numbers associated with subcellular locations indicate number of antigens identified within that subcellular location. (n=6 per extraction method).

DETAILED DESCRIPTION

1. Introduction

Figure 1:
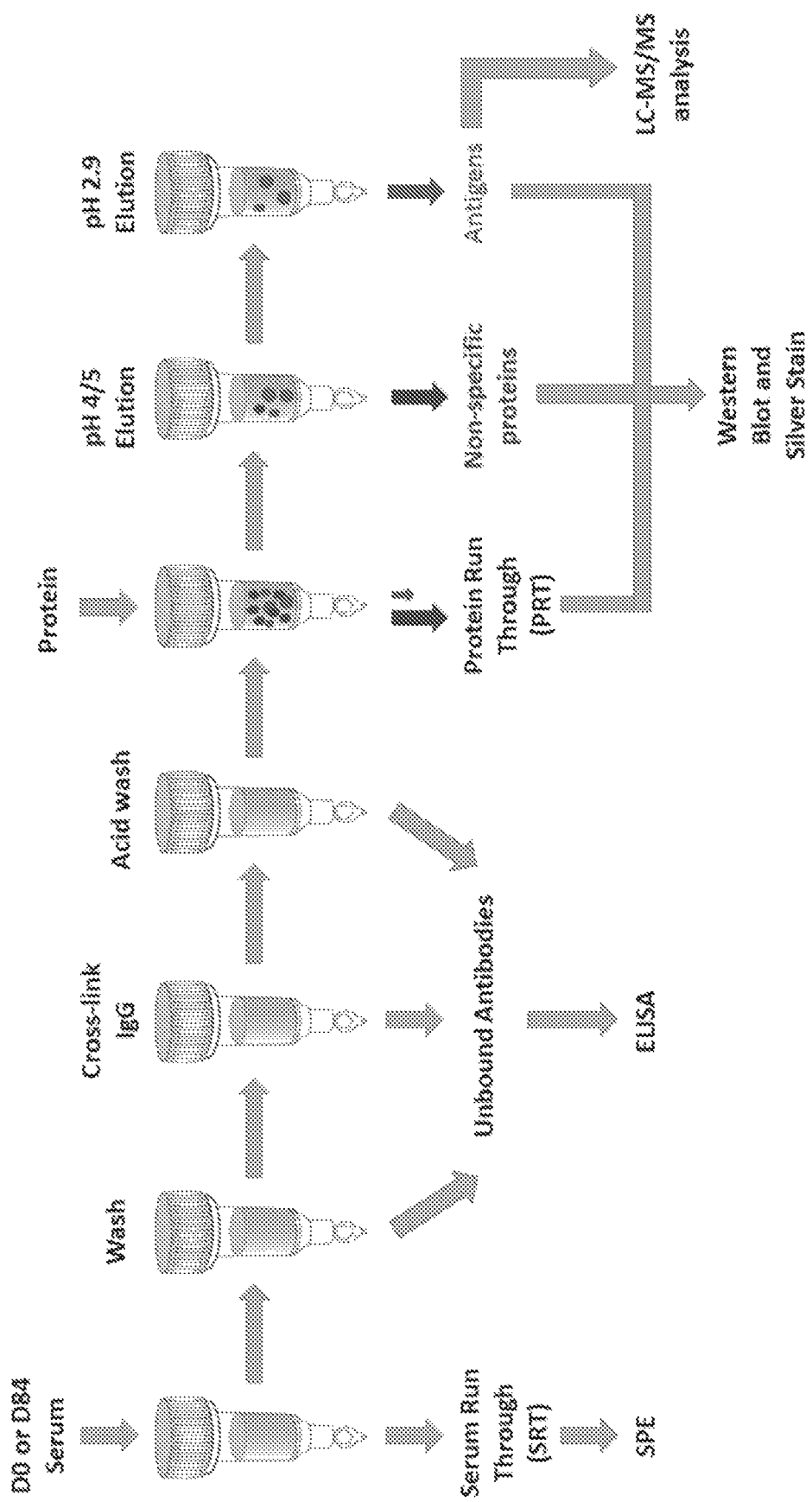
FIG. 1 illustrates a diagram of workflow for affinity chromatography column generation and validation for antigen identification. Column IgG capture following serum loading was assessed using serum protein electrophoresis (SPE). Capture and cross-linking efficiency of IgG antibodies was determined using rabbit IgG specific ELISA. Specificity of antigen capture and non-specific protein binding were assessed using silver stained gels and Western blots with post-immunization rabbit serum (D84), for protein run-through from columns eluted at pH 5, 4 and 2.9. Antigen identifications were made using LC-MS/MS analysis of specifically bound proteins eluted from D0 versus D84 columns.

Xenogeneic tissue antigenicity represents the primary barrier for expanding use of xenogeneic biomaterials in clinical practice, since recipient graft-specific immune responses are the main cause of graft rejection in both glutaraldehyde-fixed and unfixed xenogeneic tissue scaffolds. This has driven the need for high throughput methods for antigen identification in order to improve such xenogeneic biomaterials and better understand their associated recipient graft-specific immune response. Two-dimensional gel electrophoresis (2-DE) Western blots have previously been the primary immunoproteomic method for antigen identification, but are plagued by many issues. Most notably, 2-DE Western blots are time consuming, exhibit challenging reproducibility and are limited in their ability to separate highly lipophilic proteins. Shotgun proteomics has recently come to the forefront as an efficient method for maximizing protein identification, but is unable to separate proteins based on their antigenicity.

We demonstrate herein that a combined affinity chromatography shotgun immunoproteomic approach can identify antigens in clinically relevant xenogeneic biomaterials, as illustrated using bovine pericardium (BP). We show that an affinity chromatography immunoproteomic antigen identification approach can overcome the limitations of 2-DE approaches and elucidate critical characteristics of non-galactose-α1,3-galactose (non-Gal) xenoantigens. This study determines: (1) ability of an antibody affinity chromatography column to differentially capture antigenic proteins using a rabbit model of xenogeneic tissue implantation, (2) the spectrum of antigenic protein subcellular localizations available for identification using an affinity chromatography immunoproteomic antigen identification approach, and (3) the predominant subcellular locations and biologic processes in which antigens are located in a clinically applicable heart valve biomaterial (i.e., bovine pericardium).

METHODS. Pre (Day 0) and post (Day 84) immunization anti-BP serum was generated in New Zealand white rabbits. BP was subjected to two-step protein extraction process consisting of hydrophilic protein extraction (H) followed by lipophilic protein extraction (L). HP SpinTrap protein A columns were used to immobilize rabbit IgG and capture antigenic proteins from hydrophilic and lipophilic protein extracts. Affinity chromatography column antibody capture was validated using serum electrophoresis (SPE), and rabbit IgG ELISA to calculate loading and cross-linking efficiency.

Antigenicity of column eluates was assessed using Western blots. Proteins captured on D0 and D84 anti-BP columns underwent LC-MS/MS, with protein abundance compared to identify BP xenoantigens.

RESULTS. SPE indicated that the column had depleted serum of IgG, and ELISA assay showed that D0 columns had 99.99±0.0004% loading and 98.94±0.26% cross-linking, and D84 columns had 99.99±0.0005% loading and 99.08%±0.26% cross-linking efficiency. Following loading of BP protein extracts onto the resultant antibody affinity columns, both D0 and D84 columns demonstrated decreased antigenic protein content in column run-through compared to native BP protein extracts, with greater reduction in antigenic proteins in D84 columns. Silver stains and Western blots of column run-through and captured antigens confirmed that (1) non-specific binding was minimal, (2) all specifically bound proteins are antigenic, and (3) more antigens are specifically captured by D84 columns than by D0 columns. LC-MS/MS analysis resulted in identification of 133 xenoantigens, with the majority of antigens identified in NDSB-L extracts (105 antigens). Most importantly, antigens were also identified from all subcellular locations, with 18 integral membrane proteins antigens identified. Critically, isoforms of several protein families were found to be antigenic suggesting the possibility that shared epitope domains may exist. Furthermore, proteins associated with immune, coagulation and inflammatory pathways were over-represented suggestion that these biological processes play a key role in antigenicity.

CONCLUSION. This study validates a rapid, high throughput method for immunoproteomic antigen identification which overcomes the limitations of 2-DE approaches. Furthermore, important insights into the determinants of antigenicity of clinically relevant xenogeneic biomaterial (i.e., BP) are established.

The antigen identification methods described herein have many advantages over prior methods utilizing 2-DE. First, they can be performed multiplexed and in parallel, at high throughput levels. The total time to perform the approach can be 8 or fewer hours, compared to previous 2-DE Western blot methods which take at least 7 days. Second, the methods are highly reproducible; the reproducibility of the invention is much higher than methods employing 2-DE Western blots. Third, the methods are applicable to a wide range of antigens. The methods described herein can be used to identify any antigen which can be solubilized from a tissue/organ or organism, including lipophilic proteins. By comparison 2-DE gels are much more restricted in their scope as they are notoriously challenging to use for certain protein subtypes (e.g., highly lipophilic proteins). Fourth, the methods described herein reliably produce a quantitative result. In contrast, previous 2-DE approaches are semi-quantitative at best. Fifth, the herein described methods require minimal optimization between tissues. The methods described herein utilize antibodies as the primary fractionation method and therefore the variability between tissues is much less than 2-DE methods, where the protein separations are the primary fractionation method.

2. Methods

Methods for screening and identification of antigenic components of a tissue and/or an organ are provided. In varying embodiments, the methods comprise the steps of:

a) obtaining a biological sample from a subject who has been exposed to antigenic components of the tissue and/or the organ;
b) attaching immunoglobulins, or fragments thereof, from the biological sample to a stationary or solid support, thereby creating a stationary or solid phase comprising immobilized immunoglobulins, or fragments thereof;
c) extracting hydrophilic and/or lipophilic components from the tissue and/or the organ;
d) exposing the extracted components to the stationary or solid phase comprising immobilized immunoglobulins, or fragments thereof, under conditions that allow antigenic components to bind to the immunoglobulins, or fragments thereof;
e) washing the stationary or solid phase to remove unbound components;
f) eluting bound antigenic components from the immobilized immunoglobulins, or fragments thereof; and
g) identifying the bound and then eluted antigenic components by mass spectrometry.

a. Obtaining/Receiving A Biological Sample

A biological sample is obtained or received from a subject who has been exposed to antigenic components of a tissue and/or the organ or infectious agent or organism. In varying embodiments, the exposure is intrinsic. For example, the subject may be the recipient of a transplant tissue or organ, and the transplanted tissue or organ is the source of components which are antigenic to the subject. In varying embodiments, the transplanted tissue or organ can be syngeneic, allogeneic or xenogeneic. In another example, the subject may suffer from an autoimmune disease and the targeted organ or tissue in the autoimmune disease may be a source of components which are antigenic to the subject. In a further example, the subject may suffer from a cancer, and the cancerous organ or tissue may be a source of components which are antigenic to the subject. In a further example, the subject may suffer from an infectious disease, e.g., a bacterial or viral infection, and the targeted organ(s) or tissue(s) in the infectious disease may be a source of components which are antigenic to the subject.

Generally, the biological sample contains immunoglobulins. In varying embodiments, the biological sample is a fluid sample, e.g., blood, serum, plasma, saliva, urine, lymph, mucous. In varying embodiments, the biological sample is a solid tissue sample, e.g., from a transplanted tissue or organ, a cancerous tissue or organ, or from a tissue or organ targeted in an autoimmune disease.

In some embodiments, the methods further entail obtaining or receiving a control biological sample, e.g., from a subject who has not been exposed to antigenic components of a tissue and/or the organ. For example, in varying embodiments, the control biological sample can be obtained or received from a subject who has not received a transplanted tissue or organ, who does not have cancer and/or who does not suffer from an autoimmune disease.

Immunoglobulins or antibodies sufficient for immobilizing on a solid or stationary phase can be obtained in a small volume of biological sample, e.g., as little as 10 μL, 20 μL, 30 μL, 40 μL, 50 μL, 60 μL, 70 μL, 80 μL, 90 μL, 100 μL, 200 μL, 300 μL, 400 μL, 500 μL serum.

b. Attaching Antibodies To Affinity Column Stationary Phase

Immunoglobulins, or fragments thereof, from the biological sample are immobilized to a solid phase or stationary phase, e.g., for use in preparation of an immunoglobulin affinity column. In varying embodiments, immunoglobulins, or fragments thereof, from the biological sample are concentrated, isolated and/or purified. In varying embodiments, the immunoglobulins are of the IgG subclass, but in certain embodiments, immunoglobulins of the IgM, IgA, IgD, IgE subclasses may also be attached to the stationary phase of the column. In certain embodiments, immunoglobulin fragments, e.g., Fv, scFv, dsFv, Fab, Fab', F(ab')$_2$, are attached to the solid phase or stationary phase.

As appropriate or desired, the immunoglobulins from the biological sample can be concentrated, isolated and/or purified. Methods of concentrating, isolating and/or purifying immunoglobulins are known in the art, and can be used in the present methods. Such methods are described, e.g., in Harlow and Lane, "Antibodies: A Laboratory Manual," Cold Spring Harbor Laboratory Press, 1988; Harlow and Lane, "Using Antibodies: A Laboratory Manual," Cold Spring Harbor Laboratory Press, 1998; and Howard and Kaser, "Making and Using Antibodies: A Practical Handbook," Second Edition, CRC Press, 2013.

The immunoglobulins, or fragments, thereof, from the biological sample are attached to a solid phase or stationary phase to produce a stationary or solid phase comprising immobilized immunoglobulins or fragments thereof. Methods and resins, solid phase particles or stationary phases useful for attaching to immunoglobulins are known in the art and find use. In varying embodiments, resins or solid phase particles covalently bound to Protein A, Protein G, Protein A/G and/or Protein L can be used to form a strong affinity bond with the Fc portion of whole immunoglobulin molecules, e.g., IgG subclass immunoglobulins. Protein A, Protein G, Protein A/G and/or Protein L resins (e.g., agarose, sepharose) are readily commercially available, and can be purchased, e.g., from GE Life Sciences (gelifesciences.com), Thermo Fisher (fishersci.com), Sigma Aldrich (sigmaaldrich.com), BioVision (biovision.com), Dionex (dionex.com), Applied Biosystems (appliedbiosystems.com) and Bio-Rad Laboratories (bio-rad.com). In certain embodiments, the bound or attached antibodies can be further crosslinked to the Protein A or Protein G. See, e.g., Sisson, et al., *J. Immunol. Methods* (1990) 127:215-220. In varying embodiments, the immunoglobulins, or fragments thereof, are covalently attached directly to the stationary or solid phase. Techniques for covalently attaching antibodies directly onto the solid support or stationary phase are described, e.g., in Zhang, et al, *Talanta* (2010) 82:704-709; and at Thermo Fisher (tools.thermofisher.com/content/sfs/brochures/TR0005-Attach-Ab-glass.pdf). Immunoglobulin immobilization coupling chemistries of use are reviewed, e.g., in Fitzgerald, et. al, *Methods Mol Biol.* 2011; 681:35-59 and updated in Fitzgerald, et. al., *Methods Mol Biol.* 2017; 1485:27-51. Additionally, Bio-Rad Laboratories (bio-rad.com) produces activated affinity resins that can be used for directly coupling antibodies, e.g., Affi-Gel Hz hydrazide gel, which preferentially couples to the carbohydrates on the Fc portion of an immunoglobulin. In varying embodiments, whole IgG subclass antibodies are concentrated, isolated and/or purified from the biological sample using a Protein A affinity column. In varying embodiments, the stationary or solid phase is packed in a column and the same column is used for steps b)-f). In certain embodiments, the immunoglobulins or fragments thereof are directly covalently bound to the solid support or stationary phase.

c. Extracting Hydrophilic and/or Lipophilic Components

Hydrophilic and/or lipophilic components, including antigenic components, can be extracted from a tissue or organ of interest using any method known in the art. In varying embodiments, the tissue or organ of interest can be from the subject, but may be from a different subject or even a different species. Illustrative extraction methods of both water soluble and lipid soluble components from tissue are described, e.g., in Griffiths, et al., *Electrophoresis* (2008) 29(22): 4508-4515; U.S. Pat. No. 9,220,733; Intl. Publ. No. WO 2014/077934; and Wong, et al., *Acta Biomater.* (2013) 9(5):6492-501. In varying embodiments, first the hydrophilic components are extracted and then the lipophilic components are extracted.

The extracted components from organs and/or tissues refers to cells, cellular debris, proteins, nucleic acids, phospholipids, carbohydrates and other macromolecules.

The tissues or organs subject to sequential hydrophilic and lipophilic components extraction can be from any tissue or organ suspected of inducing an immune response in the subject. Generally, the tissue is live and unfixed and is minced or homogenized prior to extraction. In various embodiments, tissues subject to sequential antigen removal/decellularization include without limitation connective tissue, muscle tissue, nervous tissue (of the brain, spinal cord, and nerves), epithelial tissue, and organ tissue. Connective tissue includes fibrous tissue like fascia, tendon, ligaments, heart valves, bone, and cartilage. Muscle tissue includes skeletal muscle tissue, smooth muscle tissue, such as esophageal, stomach, intestinal, bronchial, uterine, urethral, bladder, and blood vessel tissue, and cardiac muscle tissue. Epithelial and endothelial tissue includes simple epithelial tissue, such as alveolar epithelial tissue, blood vessel endothelial tissue, and heart mesothelial tissue, and stratified epithelial tissue. In various embodiments, the tissue is subject to antigen removal is heart, heart valve, vessel, vascular conduit, artery, vein, skin, dermis, epidermis, pericardium, dura, intestinal submucosa, intestine, ligament, tendon, bone, cartilage, ureter, urinary bladder, liver, lung, thymus, spleen, kidney, umbilical cord, cornea, nerve, brain, pituitary, thyroid, parathyroid, pancreas, adrenal gland, and lymph node. The tissue may be a part of an organ or be an intact organ.

In varying embodiments tissue or organ may be from the same species as the intended recipient (e.g., is allogeneic) or from a different species from the intended recipient (e.g., is xenogeneic). In various embodiments, the tissue or organ has been or is intended to be transplanted into the subject. In varying embodiments, the tissue or organ within the subject and is cancerous or is the target of an autoimmune response. In varying embodiments, the tissue or organ is infected with an infectious agent or organism (e.g., bacterial or viral) and tissue or organ is an antigenic target secondary to the infectious disease. In various embodiments, the tissue or organ is from a porcine, ovine, bovine, ostrich (e.g., of the genus Struthio) or a non-human primate and has been transplanted or is intended to be transplanted into the subject. If the tissue or organ has been or is intended to be transplanted into the subject, a sample is taken for extraction. In varying embodiments, antigenic components are extracted from minced or homogenized tissue or organ sample at a concentration in the range of about 0.5 mg/ml to about 2.0 mg/ml, e.g., about 1.0 mg/ml. Antigenic components can be identified from small volumes of extracted hydrophilic and/or lipophilic components, e.g., as small as 100 µL, 200 µL, 300 µL, 400 µL, 500 µL. Antigenic components can be identified from small masses of tissue or organ, e.g., 500 mg, 400 mg, 300 mg, 200 mg, 100 mg, 90 mg, 80 mg, 70 mg, 60 mg, 50 mg, 40 mg, 30 mg, 20 mg, 10 mg, or less.

Generally, the minced or homogenized tissue or organ is subjected to solubilization as soon as practicable after extraction from the original host and before the tissue or organ is substantially decomposed. In various embodiments, the tissue is subjected to solubilization within 12 hours after extraction, e.g., within 10, 8, 6, 4, 3, 2, 1 hours after extraction from the original host.

i. Extracting Hydrophilic Components

Minced or homogenized tissue or organ can be contacted with (e.g., submerged in or saturated with) a solution for solubilizing the water-soluble (i.e., hydrophilic components) under sufficient conditions and for a sufficient time to extract a portion of the water soluble components from the tissue or organ to reach an equilibrium between the water-soluble components within the minced or homogenized tissue or organ and water soluble components in the solution, as appropriate. In varying embodiments, the water-soluble components are solubilized or extracted in a solution comprising a detergent or a non-detergent sulfobetaine, and further comprising one or more of a buffering agent, a reducing agent, a protease inhibitor, and one or more salts suitable for maintaining protein solubility.

In various embodiments, the minced or homogenized tissue or organ is submerged in or saturated with the solution for solubilizing the water-soluble components for at least about 0.5, 1, 2, 4, 6, 8, 10, 12, 14, 16, 18, 20, 22 or 24 hours. When unminced or larger tissue samples are used, extraction times are longer, e.g., for at least about 2, 3, 4, 5, 6, 7 days, as appropriate. The tissue or organ may be washed one or more times during the time period of submerging or saturating, e.g., to promote diffusion and separation of water-soluble components from the tissue or organ.

In various embodiments, removal of water-soluble components is performed at a temperature above freezing (e.g., above 0° C.) and at or below body temperature (e.g., at or below about 37° C.). In various embodiments, removal of water-soluble components is performed at a refrigerated temperature, e.g., between about 4-10° C. In various embodiments, removal of water-soluble components is performed at room temperature, e.g., between about 20-30° C., e.g., about 25° C. In various embodiments, removal of water-soluble components is performed at human body temperature, e.g., about 37° C.

In varying embodiments, the hydrophilic antigenic components are extracted by exposing the tissue or organ to one or more agents selected from the group consisting of a non-detergent sulfobetaine (NDSB) (e.g., NDSB-256, NDSB-201, aminosulfobetaine 14 (ASB-14), aminosulfobetaine 16 (ASB-16), 4-n-Octylbenzoylamido-propyl-dimethylammonio sulfobetaine (ASB-C8Ø), sulfobetaine 3-10, sulfobetaine 3-14, sulfobetaine 3-16, sulfobetaine 3-8, sulfobetaine 3-18), cetyltrimethylammonium bromide (CTAB), C7BzO, 0.1% sodium dodecyl sulfate (SDS), sodium octyl sulfate, Triton X-100, Triton X-114, digitonin, saponin, maltosides (e.g., n-decyl-β-D-maltopyranoside (DM), n dodecyl β-D-maltoside (DDM), 6-Cyclohexyl-1-hexyl-β-D-maltopyranoside (Cymal-6)), Brij 35, Brij 58, IGEPAL CA-630, Nonidet P40, TWEEN 20, TWEEN 40, TWEEN 60, TWEEN 80, bile salts (e.g., cholic acid, lithocholic acid, glycocholic acid, deoxycholic acid, sodium deoxycholate, 3-[(3-cholamidylpropyl)dimethylammonio]-1-propane sulfonate (CHAPS), 3-([3-cholamidopropyl]dimethylammonio)-2-hydroxy-1-propanesulfonate (CHAPSO)), cetyltrimethylammonium bromide (CTAB), urea, and thiourea.

In various embodiments, the buffering agent maintains a pH (e.g., has a pKa) to allow for solubility of the antigens in aqueous solution. For example, in some embodiments, the buffering agent maintains a pH in the range of about 4-11, e.g., a pH in the range of about 4-6, 8-11, 5-10 or 6-9. In some embodiments, the buffering agent maintains a pH of at least about 8. In some embodiments, the buffering agent maintains a pH of less than about 5. Illustrative buffering agents include without limitation Tris-HCl, phosphate, citric acid, acetate, imidazole, carbonate, IVIES, Bis-Tris, ADA, aces, PIPES, MOPSO, Bis-Tris propane, BES, MOPS, TES, HEPES, DIPSO, MOBS, TAPSO, Trizma, HEPPSO, POPSO, TEA, EPPS, Tricine, Gly-Gly, Bicine, HepBS, TAPS, AMPD, CHES, CAPSO, AMP, CAPS and CABS. These and other buffering agents of use are well-known in the art and commercially available, e.g., from Sigma-Aldrich (on the internet at sigmaaldrich.com). In some embodiments, the buffering is Tris-HCl.

In some embodiments, the one or more salts comprise a monovalent or a divalent anion. In some embodiments, the one or more salts comprise a metal halide salt. Illustrative metal halide salts of use include without limitation LiF, LiCl, LiBr, LiI, NaF, NaCl, NaBr, NaI, KF, KCl, KBr, KI, RbF, RbCl, RbBr, RbI, CsF, CsCl, CsBr, CsI, $BeF_2$, $BeCl_2$, $BeBr_2$, $BeI_2$, $MgF_2$, $MgCl_2$, $MgBr_2$, $MgI_2$, $CaF_2$, $CaCl_2$, $CaBr_2$, $CaI_2$, $SrF_2$, $SrCl_2$, $SrBr_2$, $SrI_2$, $BaF_2$, $BaCl_2$, $BaBr_2$, $BaI_2$, and mixtures thereof. In some embodiments, the one or more salts comprise KCl. In various embodiments, the one or more salts are included at a concentration of at least about 10 mM, 20 mM, 30 mM, 40 mM, 50 mM, 75 mM, or 100 mM, for example, at least about 150 mM, 200 mM, 250 mM, 300 mM, 350 mM, 400 mM, 450 mM, 500 mM. 600 mM, 700 mM, 800 mM, 900 mM or 1000 mM, for example, in the range of about 100-500 mM or about 100-200 mM.

Illustrative reducing agents for use in the solution for solubilizing the water-soluble components include without limitation Tributylphosphine (TBP), beta mercaptoethanol, 2-mercaptoethylamine, tris(2-carboxyethyl)phosphine (TCEP), cysteine-HCl, and dithiothreitol (DTT). In some embodiments, the reducing agent is DTT.

Illustrative protease inhibitors for use in the solution for solubilizing the water-soluble components include without limitation aspartic protease inhibitors, cysteine protease inhibitors, metalloprotease inhibitors, serine protease inhibitors (serpins), threonine protease inhibitors, trypsin inhibitors, and mixtures thereof. In various embodiments, the protease inhibitor is an I9, I10, I14, I24, I29, I34, I36, I42, I48, I53, I67, I68, I78 inhibitor, or a mixture thereof. In some embodiments, the protease inhibitor is AEBSF (4-(2-Aminoethyl) benzenesulfonyl fluoride hydrochloride), also sold as PEFABLOC®. In some embodiments, the protease inhibitor is Phenylmethylsulfonyl fluoride (PMSF). Numerous protease inhibitor cocktails of use are commercially available from Roche Molecular Biochemicals.

In some embodiments, the water-soluble components are solubilized in a solution that comprises a chelation agent. Illustrative chelation agents include without limitation ethylenediaminetetraacetic acid (EDTA), diethylenetriaminepentaacetic acid (DTPA), Citric Acid, N,N-bis(carboxymethyl)glycine (NTA), and the meso isomer of Dimercaptosuccinic acid (DMSA).

In some embodiments, the water-soluble components are solubilized in a solution that does not comprise an amphiphile. In some embodiments, the water-soluble components are solubilized in a solution that does not comprise a detergent. In some embodiments, the water-soluble components are solubilized in a solution that comprises a non-detergent sulfobetaine. Illustrative non-detergent sulfobetaines include without limitation NDSB-256, NDSB-211, NDSB-195, NDSB-221 and NDSB-201.

In some embodiments, the water-soluble components are solubilized in a solution comprising Tris-HCl, dithiothreitol (DTT), a protease inhibitor, and KCl. In a particular embodiment, the water-soluble components are solubilized in a solution comprising 10 mM Tris-HCl, 100 mM DTT, 100 mM KCl and 2 mM MgCl$_2$. A protease inhibitor and/or an antibacterial agent and/or an antifungal agent may also be included.

ii. Extracting Lipophilic Components

In certain embodiments, the minced or homogenized tissues or organs that have been subject to extraction and separation of water-soluble antigens can subsequently be subject to extraction of lipid-soluble (i.e., lipophilic) components. In other embodiments, tissues or organs are first subject to extraction of lipid soluble components and second subject to extraction of water-soluble antigens. In some embodiments, the lipophilic components are solubilized or extracted in a solution comprising a detergent or non-detergent sulfobetaine, e.g., at a concentration that is at least about 5-fold, e.g., at least about 6-fold, 7-fold, 8-fold, 9-fold, 10-fold, or more, of the concentration of agent used or necessary to extract hydrophilic antigenic components. The lipophilic extraction solution may further comprise one or more of a buffering agent, a reducing agent, a protease inhibitor, one or more salts suitable for maintaining protein solubility and an amphiphile.

The minced or homogenized tissue or organ can be saturated with (e.g., submerged in or saturated with) a solution for solubilizing the lipid-soluble components for a sufficient time to extract a portion of the lipid soluble components from the tissue or organ or to reach an equilibrium between the lipid-soluble components within the tissue or organ and lipid soluble components in the solution, as appropriate.

In various embodiments, the minced or homogenized tissue or organ is saturated with (e.g., submerged in or saturated with) the solution for solubilizing the lipid-soluble components for at least about 0.5, 1, 2, 4, 6, 8, 10, 12, 14, 16, 18, 20, 22 or 24 hours. When unminced or larger tissue samples are used, extraction times are longer, e.g., for at least about 2, 3, 4, 5, 6, 7 days, as appropriate. The tissue or organ may be washed one or more times during the time period of submerging or saturating, e.g., to promote diffusion and separation of lipid-soluble components from the tissue or organ.

In various embodiments, removal of lipid-soluble components is performed at a temperature above freezing (e.g., above 0° C.) and at or below body temperature (e.g., at or below about 37° C.). In various embodiments, removal of lipid-soluble components is performed at a refrigerated temperature, e.g., between about 4-10° C. In various embodiments, removal of lipid-soluble components is performed at room temperature, e.g., between about 20-30° C., e.g., about 25° C. In various embodiments, removal of lipid-soluble components is performed at human body temperature, e.g., about 37° C.

In varying embodiments, the lipophilic antigenic components are extracted by exposing the tissue or organ to one or more agents selected from the group consisting of a non-detergent sulfobetaine (NDSB) (e.g., NDSB-256, NDSB-201, aminosulfobetaine 14 (ASB-14), aminosulfobetaine 16 (ASB-16), 4-n-Octylbenzoylamido-propyl-dimethylammonio sulfobetaine (ASB-C8Ø), sulfobetaine 3-10, sulfobetaine 3-14, sulfobetaine 3-16, sulfobetaine 3-8, sulfobetaine 3-18), cetyltrimethylammonium bromide (CTAB), C7BzO, 1.0% sodium dodecyl sulfate (SDS), sodium octyl sulfate, Triton X-100, Triton X-114, digitonin, saponin, maltosides (e.g., n-decyl-β-D-maltopyranoside (DM), n dodecyl β-D-maltoside (DDM), 6-Cyclohexyl-1-hexyl-β-D-maltopyranoside (Cymal-6)), Brij 35, Brij 58, IGEPAL CA-630, Nonidet P40, TWEEN 20, TWEEN 40, TWEEN 60, TWEEN 80, bile salts (e.g., cholic acid, lithocholic acid, glycocholic acid, deoxycholic acid, sodium deoxycholate, 3-[(3-cholamidylpropyl)dimethylammonio]-1-propane sulfonate (CHAPS), 3-([3-cholamidopropyl]dimethylammonio)-2-hydroxy-1-propanesulfonate (CHAPSO)), cetyltrimethylammonium bromide (CTAB), urea, and thiourea, wherein the lipophilic antigenic components are extracted by exposing the tissue or organ to a concentration of agent that is at least about 5-fold, e.g., at least about 6-fold, 7-fold, 8-fold, 9-fold, 10-fold, or more, of the concentration of agent used or necessary to extract hydrophilic antigenic components. In varying embodiments, the lipophilic antigenic components are extracted by exposing the tissue or organ to non-detergent sulfobetaine 256 plus n-dodecyl-β-D-maltoside. In varying embodiments, the lipophilic antigenic components are extracted by exposing the tissue or organ to a cyclodextrin derivative, a high molecular weight pullulan, or mixtures thereof.

In various embodiments, the amphiphile is a zwitterionic detergent. In some embodiments, the amphiphile is a sulfobetaine. Illustrative sulfobetaines of use include without limitation 3-[4N,N-Dimethyl(3-myristoylaminopropyl)ammonio]propanesulfonate (amidosulfobetaine-14; ASB-14); amidosulfobetaine-16 (ASB-16); 4-n-Octylbenzoylamido-propyl-dimethylammonio sulfobetaine (ASB-C8Ø); 3-(N, N-Dimethyloctylammonio) propanesulfonate inner salt (SB3-8); N-Decyl-N,N-dimethyl-3-ammonio-1-propanesulfonate (SB 3-10), N-Decyl-N,N-dimethyl-3-ammonio-1-propanesulfonate (SB 3-12), N-Tetradecyl-N,N-dimethyl-3-ammonio-1-propanesulfonate (SB 3-14); 3-(N,N-Dimethylpalmitylammonio) propanesulfonate (SB3-16); 3-(N,N-Dimethyloctadecylammonio) propanesulfonate (SB3-18); 3-(1-Pyridinio)-1-propanesulfonate (NDSB-201); 3-(Benzyldimethylammonio) propanesulfonate (NDSB-256); NDSB-211, NDSB-195, NDSB-221; 3-[(3-Cholamidopropyl)dimethylammonio]-1-propanesulfonate (CHAPS), and 3-[(3-Cholamidopropyl)dimethylammonio]-2-hydroxy-1-propanesulfonate (CHAPSO). In various embodiments, the sulfobetaine is an amidosulfobetaine. Illustrative amidosulfobetaines include without limitation, ASB-14, ASB-16 and ASB-C8Ø. In various embodiments, the sulfobetaine is a non-detergent sulfobetaine. Illustrative non-detergent sulfobetaines include without limitation NDSB-256, NDSB-211, NDSB-195, NDSB-221 and NDSB-201.

In various embodiments, the buffering agent maintains a pH (e.g., has a pKa) to allow for solubility of the antigens in aqueous solution. For example, in some embodiments, the buffering agent maintains a pH in the range of about 4-11, e.g., a pH in the range of about 4-6, 8-11, 5-10 or 6-9. In some embodiments, the buffering agent maintains a pH of at least about 8. Illustrative buffering agents include without limitation Tris-HCl, phosphate, citric acid, acetate, imidazole, carbonate, IVIES, Bis-Tris, ADA, aces, PIPES, MOPSO, Bis-Tris propane, BES, MOPS, TES, HEPES, DIPSO, MOBS, TAPSO, Trizma, HEPPSO, POPSO, TEA, EPPS, Tricine, Gly-Gly, Bicine, HepBS, TAPS, AMPD, CHES, CAPSO, AMP, CAPS and CABS. These and other buffering agents of use are well-known in the art and commercially available, e.g., from Sigma-Aldrich (on the internet at sigmaaldrich.com). In some embodiments, the buffering is Tris-HCl.

In some embodiments, the one or more salts comprise a monovalent or a divalent anion. In some embodiments, the one or more salts comprise a metal halide salt. Illustrative metal halide salts of use include without limitation LiF, LiCl, LiBr, LiI, NaF, NaCl, NaBr, NaI, KF, KCl, KBr, KI, RbF, RbCl, RbBr, RbI, CsF, CsCl, CsBr, CsI, BeF$_2$, BeCl$_2$, BeBr$_2$, BeI$_2$, MgF$_2$, MgCl$_2$, MgBr$_2$, MgI$_2$, CaF$_2$, CaCl$_2$, CaBr$_2$, CaI$_2$, SrF$_2$, SrCl$_2$, SrBr$_2$, SrI$_2$, BaF$_2$, BaCl$_2$, BaBr$_2$, BaI$_2$, and mixtures thereof. In some embodiments, the one or more salts comprise KCl. In various embodiments, the one or more salts are included at a concentration of at least about 50 mM, 75 mM, or 100 mM, for example, at least about 150 mM, 200 mM, 250 mM, 300 mM, 350 mM, 400 mM, 450 mM or 500 mM.

Illustrative reducing agents for use in the solution for solubilizing the lipid-soluble components include without limitation Tributylphosphine (TBP), beta mercaptoethanol, 2-mercaptoethylamine, tris(2-carboxyethyl)phosphine (TCEP), cysteine-HCl, and dithiothreitol (DTT). In some embodiments, the reducing agent is DTT.

Illustrative protease inhibitors for use in the solution for solubilizing the lipid-soluble components include without limitation aspartic protease inhibitors, cysteine protease inhibitors, metalloprotease inhibitors, serine protease inhibitors (serpins), threonine protease inhibitors, trypsin inhibitors, and mixtures thereof. In various embodiments, the protease inhibitor is an I9, I10, I14, I24, I29, I34, I36, I42, I48, I53, I67, I68, I78 inhibitor, or a mixture thereof. In some embodiments, the protease inhibitor is AEBSF (4-(2-Aminoethyl) benzenesulfonyl fluoride hydrochloride), also sold as PEFABLOC®. In some embodiments, the protease inhibitor is Phenylmethylsulfonyl fluoride (PMSF). Numerous protease inhibitor cocktails of use are commercially available from Roche Molecular Biochemicals.

In some embodiments, the lipid-soluble components are solubilized in a solution that comprises one or more of an antibacterial agent and/or an antifungal agent.

In some embodiments, the lipid-soluble components are solubilized in a solution that comprises a chelation agent. Illustrative chelation agents include without limitation ethylenediaminetetraacetic acid (EDTA), diethylenetriaminepentaacetic acid (DTPA), Citric Acid, N,N-bis(carboxymethyl)glycine (NTA), and the meso isomer of Dimercaptosuccinic acid (DMSA).

In some embodiments, the lipid-soluble components are solubilized in a solution comprising Tris-HCl, dithiothreitol (DTT), a protease inhibitor, KCl and ASB-14. In a particular embodiment, the lipid-soluble components are solubilized in a solution comprising 10 mM Tris-HCl, 100 mM DTT, 100 mM KCl, 2 mM MgCl$_2$ and 1-4% ASB-14. A protease inhibitor and/or an antibacterial agent and/or an antifungal agent may also be included.

d. Exposing Extracted Components to Immobilized Antibodies

The extracted or solubilized hydrophilic and/or lipophilic components are exposed to the stationary or solid phase comprising immobilized immunoglobulins, or fragments thereof, under conditions that allow antigenic components to bind to the immunoglobulins, or fragments thereof. If extracted separately, the extracted or solubilized hydrophilic and lipophilic components can be pooled prior to exposure to the immobilized immunoglobulins, or fragments thereof. Generally, this step can be performed at neutral range pH and an isotonic range salt concentration. In varying embodiments, extracted or solubilized hydrophilic and/or lipophilic components are exposed to the stationary or solid phase comprising immobilized immunoglobulins at a pH in the range of about 6 to about 8, e.g., at pH 6.0, 6.5, 7.0, 7.5, 8.0. In varying embodiments, extracted or solubilized hydrophilic and/or lipophilic components are exposed to the stationary or solid phase comprising immobilized immunoglobulins at a salt concentration in the range of about 100 mM to about 250 mM, e.g., about 100 mM, 110 mM, 120 mM, 130 mM, 140 mM, 150 mM, 160 mM, 170 mM, 180 mM, 190 mM, 200 mM, 210 mM, 220 mM, 230 mM, 240 mM or 250 mM. Generally, In varying embodiments, this step can be performed at a temperature between 4° C. to about 30° C. In some embodiments, binding of the extracted antigenic components is performed at room temperature, e.g., in the range of about 20° C. to about 25° C. Generally, the higher the temperature, the shorter the incubation time that is needed. For example, when performed at room temperature, exposure for 30, 40, 50, 60, 70, 80, 100, 110, or 120 minutes is generally sufficient. Conversely, when performed at a cooler temperature, longer incubation times should be allowed. For example, when performed at a refrigerated temperature (e.g., about 4° C.), the incubation can be left overnight, or about 8 hours.

To facilitate binding of the antigenic components within the extracted or solubilized hydrophilic and/or lipophilic components to the immobilized immunoglobulins, or fragments thereof, the stationary phase is agitated during the exposure incubation. For example, if the stationary or solid phase is in batch form, the stationary or solid phase can be stirred or repetitively inverted. If the stationary or solid phase is packed in a column, the column can be repetitively inverted (e.g., end-over-end rotation).

e. Washing the Stationary or Solid Phase to Remove Unbound Components

Extracted or solubilized hydrophilic and/or lipophilic components that do not bind to the immobilized immunoglobulin are separated from the stationary or solid phase comprising the immobilized immunoglobulin, or fragments thereof. This washing step can be accomplished using any method known in the art. For example, the stationary or solid phase can be washed in the same buffer used for binding of extracted components (e.g., neutral range pH and isotonic range salts) and then separated from the wash buffer, e.g., using centrifugation or by flowing wash buffer through a column packed with the stationary or solid phase comprising the immobilized immunoglobulin. The stationary or solid phase comprising the immobilized immunoglobulin is washed until no further unbound extracted or solubilized hydrophilic and/or lipophilic components can be detected or until the extracted or solubilized hydrophilic and/or lipophilic components are below a predetermined threshold level.

f. Eluting Antigenic Components Bound to Immobilized Immunoglobulins, or Fragments Thereof Antigenic components bound to immobilized immunoglobulin, or fragments thereof, can be eluted from the stationary or solid phase using any method known in the art. Strategies for elution of antigenic components bound to antibodies include adjusting one or more parameters to disfavor binding, including without limitation, increasing or decreasing pH, increasing salt, or increasing acetonitrile concentrations. The adjusted parameter can be increased step-wise or via a gradient. In varying embodiments, the antigenic components are eluted from binding to the immobilized immunoglobulins, or fragments thereof, by reducing the pH first to about pH 5, then to about pH 4 to elute weak or non-specifically binding components, and finally to about pH 2.9-3.0 to elute specifically binding antigenic components. In varying embodiments, the specifically binding antigenic components can be eluted into tubes comprising a small volume of buffered alkaline solution, e.g., a buffered solution of at least about pH 8.0, in order to neutralize the environment of the eluted antigenic components.

g. Identifying the Eluted Antigenic Components by Mass Spectrometry

The eluted antigenic components are then identified by mass spectrometry. Any mass spectrometry methodology known in the art can be used. In varying embodiments, the antigenic components are subject to liquid chromatography-tandem mass spectrometry (LC-MS/MS). In certain embodiments, the antigenic components are subject to matrix-assisted laser desorption/ionization (MALDI) or surface-enhanced laser desorption/ionization (SELDI). In certain embodiments, extracted proteinaceous antigenic components are subjected to proteolytic cleavage, e.g., digestion with a protease under sufficient conditions to cleave extracted proteins into peptides. Proteases that cleave discriminately at certain amino acid residues or within specific amino acid sequence motifs find use. Illustrative proteases of use in the preparation of peptides for mass spectrometry analysis include, e.g., Trypsin, Lys-C, and Lys-N (Gershon, *J Proteome Res*. (2014) 13(2):702-9). Enzyme mixtures for preparation of peptides for mass spectrometric analysis are commercially available, e.g., from Promega (promega.com). In varying embodiments, the protease to protein mass ratio can be in the range of 1:12.5 to 1:50, e.g., 1:25. The cleaved peptides can be desalted and separated, e.g., using liquid chromatography (e.g., HPLC, UPLC, UHPLC) before being subjected to mass spectrometry (e.g., tandem mass spectrometry) to generate a peptide mass fingerprint (PMF). The PMF data is searched against protein sequence databases, e.g., Uniprot and Fasta. Post-translational modifications (PTMs), cleavage sites, common contaminants and reverse sequences are accounted for before making the final protein identifications. Identified proteins can be further validated, e.g., using a Gaussian linearized model.

EXAMPLES

The following examples are offered to illustrate, but not to limit the claimed invention.

Example 1

Determination of Xenogeneic Heart Valve Biomaterial Antigenicity Using an Affinity Chromatography Immunoproteomic Approach Materials and Methods All chemicals were purchased from Sigma-Aldrich (St. Louis, MO) unless otherwise stated.

Tissue Harvest.

Fresh BP was harvested immediately postmortem from young adult cattle (Spear Products, Coopersburg, PA, USA) and shipped on dry ice. Tissue was defrosted and washed in 0.1% (w/v) anhydrous ethylenediaminetetraacetic acid (EDTA), 1% (v/v) antibiotic and antimycotic solution (AAS), phosphate-buffered saline (PBS) (pH 7.4) and 4% (v/v) Tris-HCl (pH 8.0). Tissue underwent dissection to remove connective tissue, and the pericardial sac was cut into 1×16 cm circumferential strips individually stored in Dulbecco's Modified Eagles Medium (DMEM) with 15% (v/v) dimethyl sulfoxide (DMSO) at −80° C. (58).

Anti-Bovine Pericardium Serum Production.

All experimental procedures and protocols were approved by the University of California, Davis Institutional Animal Care and Use Committee (IACUC) and performed in accordance with the relevant guidelines and regulations from the Guide for the Care and Use of Laboratory Animals (59) New Zealand white rabbits (n=2) received subcutaneous injections of 500 µL of homogenized native BP (1 g BP in 5 mL of 10 mM Tris-HCl (pH 8.0), 1 mM dithiothreitol (DTT), 2 mM magnesium chloride hexahydrate ($MgCl_2$—$6H_2O$), 10 mM potassium chloride (KCl), 0.5 mM Pefabloc (Roche, Indianapolis, IN)) and Freund's adjuvant at a 1:1 ratio at D0, 14, 28, 42 (58). Blood was collected on D84, centrifuged at 3000 g, with resultant anti-native BP serum stored at −80° C.

Native Bovine Pericardium Protein Extraction.

A two-step extraction process was carried out with hydrophilic protein extraction (H) followed by lipophilic protein extraction (L); using either 134 mM non-detergent sulfobetaine 256 (NDSB-256) (NDSB-H) and 1% n-dodecyl-β-D-maltoside (NDSB-L), or 0.1% (w/v) sodium dodecyl sulfate (SDS) (SDS-H) and 1% (w/v) SDS (SDS-L).

Protein was extracted from minced native BP as previously described (58). Briefly, minced BP (0.2 g) was incubated in 1 mL standard extraction solution (10 mM tris-HCl (pH 8.0), 1 mM DTT, 2 mM $MgCl_2$—6H2O, 10 mM KCl, 0.5 mM Pefabloc) containing either (1) 134 mM NDSB-256 or (2) 0.1% (w/v) SDS (Bio-Rad, Hercules, CA) representing the two hydrophile extraction solutions. Samples were subjected to 1,000 rpm, 4° C. for 1 h and then centrifuged at 17,000 g, 4° C. for 25 min. Supernatant was collected and defined as NDSB-H and SDS-H respectively. The insoluble pellet washed twice by resuspension in 1 mL hydrophile extraction solution at 1,400 rpm, 4° C. for 30 min and centrifuged at 17,000 g, 4° C. for 25 min. Supernatant was discarded during wash steps. Washed pellets were then incubated in 0.5 mL lipophile extraction solution containing either (1) 134 mM NDSB-256 and 1% (w/v) n-dodecyl-β-D-maltoside, for NDSB pellets or (2) 1% (w/v) SDS for SDS pellets. Samples were subjected to 1,400 rpm, 4° C. for 1 h and then centrifuged at 17,000 g, 4° C. for 25 min. Supernatant was collected, defined as NDSB-L and SDS-L respectively, and stored at −80° C. Protein concentrations were measured using DC Protein Assay (Bio-rad, Hercules, CA) and protein percent yield was calculated by dividing total protein extracted (mg) by sample weight (mg) and multiplying by 100.

Affinity Chromatography.

Rabbit IgG antibodies were isolated from whole serum using a Protein A HP SpinTrap (GE Healthcare, Pittsburgh PA) according to the manufacturer's antibody capture and cross-linking protocol. The resultant rabbit anti-native BP affinity columns were then utilized to isolate antigenic proteins from native BP protein extracts. Two different types of columns were made, one with D0 serum and one with D84 anti-BP serum. Briefly, serum was diluted 1:10 with binding buffer (50 mM Tris, 150 mM NaCl, pH 7.5), and 200 µL was incubated in the column with end-over-end rotation for 30 min. The column was then washed with 400 µL binding buffer, followed by 400 µL of 200 mM triethanolamine and cross-linked with 400 µL of 50 mM dimethyl pimelimidate dihydrochloride (DMP) in 200 mM triethanolamine for 1 h with end-over-end rotation. Columns were blocked with 400 µL of 100 mM ethanolamine, and unbound antibodies removed with 200 µL of pH 2.9 elution buffer (0.1 M glycine with 2 M urea). Columns were incubated with 200 µL of native BP protein extract for 1 h with end-over-end rotation. Bound proteins were then eluted using sequential washes with elution buffer at a pH of 5 and 4 for non-specific binding and final specific-binding elution at pH of 2.9. All washes and run-throughs were collected for later analysis and stored at −80° C.

Serum Electrophoresis.

Rabbit IgG antibodies were isolated from whole serum with Protein A HP SpinTrap columns. Native and run-through serum were submitted for serum protein electrophoresis (SPE) through IDEXX (Sacramento, CA) for qualitative assessment of serum IgG depletion (n=1).

ELISA.

Rabbit IgG ELISA SimpleStep kits were purchased from Abcam (Cambridge, MA) and used according to manufacturer's recommendations. Briefly, native serum was diluted 1:1,000,000, while post-capture and post-cross-linking column washes were diluted between 1:1-1:1,000. 50 µL of diluted samples, along with 50 µL of the proprietary Capture and Detection Antibody Cocktail were plated in triplicate in the supplied 96 well plate. Plates were incubated at room temperature (RT) for 1 h, washed 3 times (1,050 µL total) in supplied Wash Solution. 100 µL of Start Solution was added for 3 min and then quenched with 100 µL Stopping Solution. Plate absorbance was read at 450 nm. Column IgG loading capacity was determined as the amount of antibody in native serum minus the amount present in column run-through serum. Column cross-linking efficiency was determined as the percentage of bound antibodies remaining on the column following post-binding and post-cross-linking wash steps. Column binding capacity and cross-linking efficiency were determined using columns for D0 and D84 serum (n=6 per timepoint), and n=3 of technical replicates per wash.

One-Dimensional Electrophoresis, Western Blot, and Silver Stain.

Native BP protein extract, protein run-through and all eluates from D0 and D84 columns were assessed using one-dimensional SDS-page gels and Western blot as previously reported (n=4 per column and protein extraction method) (13,58). All blots were probed with D84 serum (1:100 dilution) and assessed for IgG positivity using HRP-conjugated mouse anti-rabbit secondary (1:5,000 dilution) (Jackson ImmunoResearch, West Grove, PA, USA). Additional SDS-page gels were silver stained with a modified acidic silver staining protocol (Silver Stain PlusOne, AmershamPharmacia) (n=4) (13).

Proteomic Analysis.

Proteins eluted from columns during the specific-binding pH 2.9 elution step were submitted to the University of California, Davis Proteomics Core and subjected to LC-MS/MS analysis. Following proteolytic digestion at a 1:25 ratio of Lys-C/trypsin (Promega) and protein, 550 µL of ammonium bicarbonate was added to dilute urea and activate trypsin overnight at 37° C. Samples were then subject to liquid chromatography-mass spectrometry on a Exactive Plus Orbitrap Mass Spectrometer (Thermo Scientific) in conjunction with an EASY-nLC II nano UHPLC, a 75 micron, 150 mm silica column filled with Magic C18 200A 3U, and Proxeon nanospray source. Tandem mass spectra were extracted and charge state deconvoluted with IDPicker 2.0, which included a cRAP database of common laboratory contaminants and an equal number of reverse protein sequences (n=6). Distribution of subcellular locations and biological processes of identified antigenic proteins were investigated using Uniprot database (16)

Statistical Analysis.

Proteomic data was analyzed using Guassian linearized modeling to determine the differential abundance of proteins between the groups as previously reported (60). Antigenic proteins were defined as those proteins isolated with statistically greater abundance from D84 columns versus D0 columns. A paired, two-tailed Student's t-test was used to find significance between groups within the ELISA assay. Groups were considered significantly different when p<0.05. Protein extraction yields were analyzed using one-way analysis of variance (ANOVA) with Tukey HSD post-hoc test and statistical significance defined at p<0.05. All values represent the mean±s.d.

Results

IgG Binding and Cross-Linking Efficiency.

Figure 2:
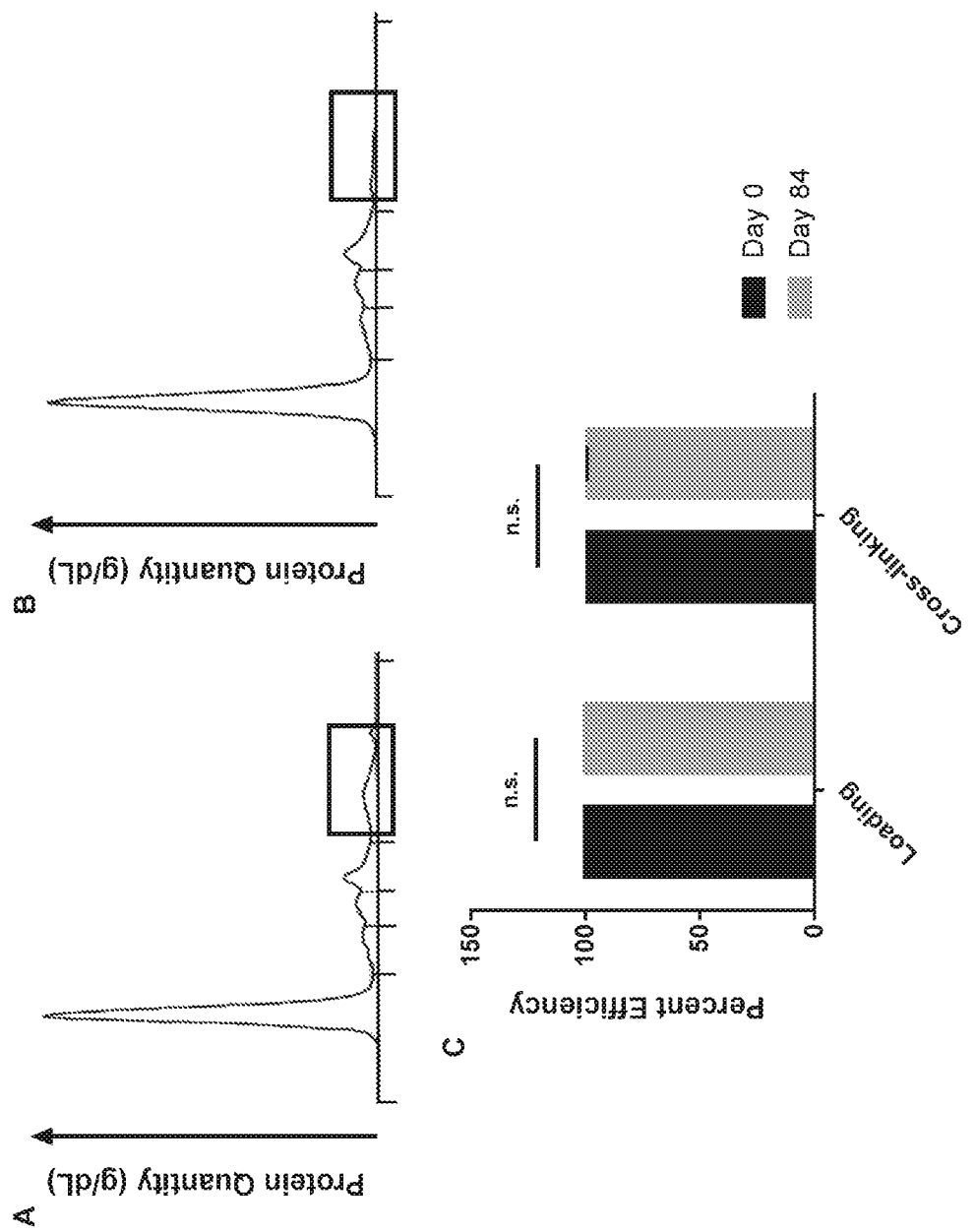
FIGS. 2A-C illustrate assessment of column IgG binding capacity and cross-linking efficiency. Serum protein electrophoresis (SPE) of native rabbit serum showing IgG levels (a). Column run-through following D84 anti-native BP rabbit serum loading on SpinTrap Column (b). Boxes indicate the gamma peak, containing IgG along with fibronectin and C-reactive protein. Gamma peak was reduced from 0.3 mg/dL in native serum to below 0.1 mg/dL in the run-through (n=1). Calculated efficiency of rabbit IgG capture and cross-linking to the column determined by ELISA analysis of IgG content in native serum and column run-through (c). No difference in IgG capture or cross-linking efficiency was found between D0 versus D84 serum using a paired two-tailed Student's t-test (n=6 per timepoint, p=0.4663, values represent the mean±s.d.).

Efficiency of IgG binding and cross-linking to SpinTrap columns was confirmed by performing serum protein electrophoresis (SPE) and IgG ELISA. SPE demonstrated reduction in gamma peak of run-through serum, while all other SPE peaks were unchanged (FIGS. 1a and 1b). To further confirm and quantify column IgG binding capacity and cross-linking efficiency, rabbit IgG ELISA was run on serum, column run-through, and all subsequent wash steps from rabbits exposed to native BP at day 0 (D0) and day 84 (D84) post-immunization. Both D0 and D84 columns demonstrated a binding capacity of 99.99% (99.99±0.0004% vs 99.99±0.0005% respectively) of the IgG in native serum. By subtracting the IgG lost during subsequent washes from the amount initially bound to the column, cross-linking efficiency was calculated at 98.94±0.26% for D0 and 99.08%±0.26% for D84 columns. Cross-linking and loading for D0 and D84 were not significantly different (n=6, p=0.4663). See, FIG. 2.

Figure 3:
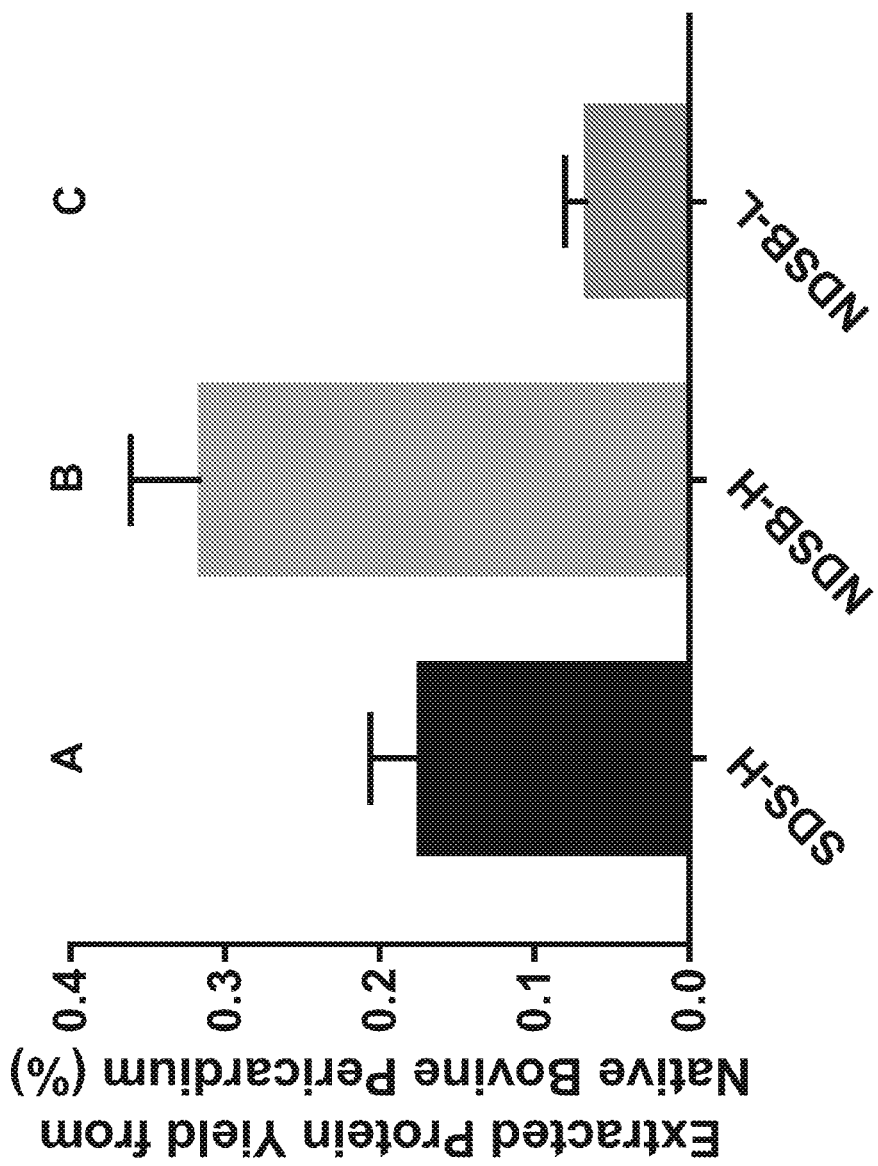
FIG. 3 illustrates native BP protein extraction % yield achieved using each extraction method. Percent yield of protein extraction for 0.1% (w/v) SDS (SDS-H), 134 mM non-detergent sulfobetaine-256 (NDSB-H), and 134 mM non-detergent sulfobetaine-256 combined with 1% (w/v) n-dodecyl-β-D-maltoside (NDSB-L). NDSB-L yields statistically less protein from native BP than either NDSB-H or SDS-H. All data are expressed as mean±s.d. and were analyzed using one-way analysis of variance (ANOVA) with Tukey HSD post-hoc test and statistical significance defined at p<0.05 (n=8 for SDS and n=10 for NDSB extraction methods, p<0.0001).

Validation of Specificity of Antigenic Protein Capture in the Affinity Column. Western blotting was used for initial validation and visualization of specificity of antigen capture and elution from the affinity column. 1% (w/v) sodium dodecyl sulfate lipophilic (SDS-L) extracts resulted in Western blots with no apparent antigen capture. Consequently, only 134 mM non-detergent sulfobetaine-256 hydrophilic (NDSB-H), 1% (w/v) n-dodecyl-β-D-maltoside lipophilic (NDSB-L) and 0.1% (w/v) sodium dodecyl sulfate hydrophilic (SDS-H) extracts were utilized for later LC-MS/MS identification experiments. Percent protein yield was significantly lower in NDSB-L extracts (0.0655±0.015%) than either NDSB-H (0.3152±0.046%) or SDS-H (0.1735±0.033%) (p<0.05) (FIG. 3).

NDSB-H, NSDB-L and SDS-H were incubated in D0 and D84 SpinTrap columns and subsequent protein run-through and eluates were collected. Protein run-through from D0 columns demonstrated minimal reduction in antigenic band intensity compared to native BP protein extract (FIG. 4a), indicating that antigen capture in the column was minimal. There was a greater capture of antigenic proteins in D84 columns compared to D0 columns, as demonstrated by the greater reduction in band intensity of protein run-through from D84 columns (FIG. 4a and FIG. 5).

To determine if captured proteins were specifically bound to both D0 and D84 columns, stepwise pH elution was undertaken. Silver staining of eluates from both columns demonstrated minimal protein elution for pH 5 and 4 eluates, with elution of specifically captured proteins in pH 2.9 eluates (FIG. 4b and FIG. 5b). Western blot analysis demonstrated that no antigenic proteins eluted off either column with washes at pH 5 and 4, but when the column was washed at pH 2.9 bound antigens were eluted (FIG. 4b and FIG. 5a).

Finally, antigenic proteins eluted from D0 versus D84 were compared to determine if antigen capture was increased in columns generated using post-immunization serum compared to pre-immunization serum. D84 pH 2.9 eluate contained many more antigenic protein bands than the D0 pH 2.9 eluate, which identified virtually no antigenic protein bands (FIG. 4c and FIG. 5a). This process was repeated for all four native protein extract types to confirm specificity of antigen capture for each extraction.

Antigen Identification Efficiency.

Figure 7:
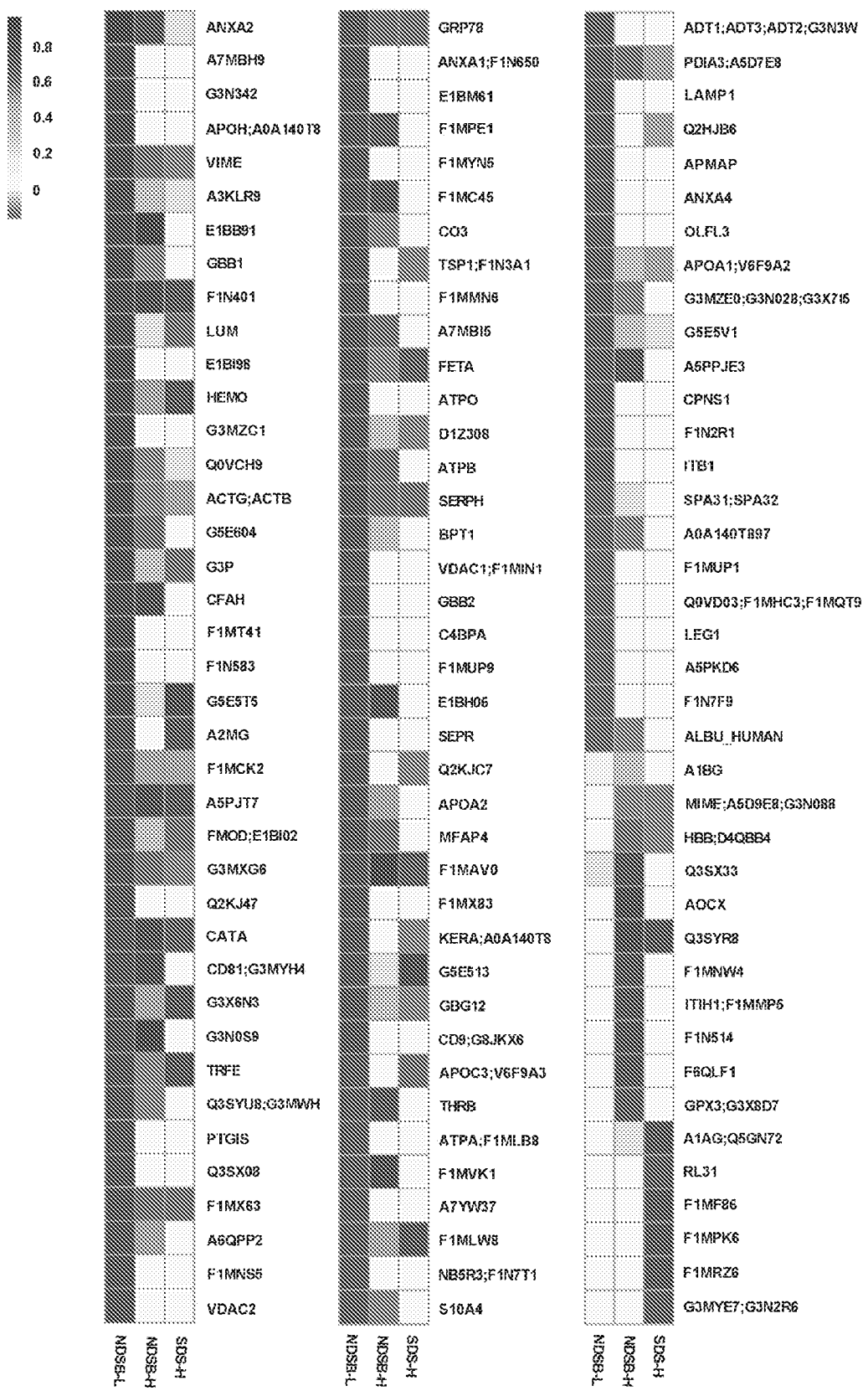
FIG. 7 illustrates a heatmap of the statistically significant antigenic protein identifications within each extraction method. Antigens were predominantly identified in NDSB-L, but alternative extraction methods are required to optimize total number of antigens identified. Scale is a Log of the fold change. Proteomic data was analyzed using Guassian linearized modeling to determine the differential abundance of proteins between the groups as previously reported (60) White squares indicate that the protein was not present in that sample. (n=6 per extraction method). Groups were considered significantly different when p<0.05.

Mass spectrometry data were analyzed to identify antigenic proteins, and efficiency of antigen identification was examined between protein extraction methods. A total of 133 antigens were identified in native BP (FIGS. 6 and 7). Despite having the lowest yield of extracted native BP protein (FIG. 3), NDSB-L protein extracts identified the greatest number of antigens (105), while NDSB-H identified 47 and SDS-H only 35 (FIG. 6a). Furthermore, NDSB-L extracts resulted in identification of 63 unique antigens not present in any other extract. Unique antigen identifications were less commonly found with NDSB-H (12 unique identifications) and SDS-H (15 unique identifications) extracts. Eleven of the 133 identified antigens were identified using all three extraction methods. Both hydrophilic fractions contained antigens which were also present in NDSB-L extracts, whereas only a single identified antigen was found in both NDSB-H and SDS-H (Immunoglobulin J Chain). Unsurprisingly, more antigens were shared between NDSB-H and NDSB-L.

Distribution of subcellular locations and biological processes of identified antigenic proteins were investigated using Uniprot database (FIG. 6b-6d).16 Although antigenic proteins were identified from all tissue compartments and subcellular locations, some locations were overrepresented in terms of their antigen content. Overall, 74.2% of antigens were located in the secretions, cell membrane, cytoplasm, and matrix. Importantly, 66% of the identified cell membrane antigens were integral membrane proteins (18 antigens). Of the remaining antigens, 9% came from the nuclear compartment and endoplasmic reticulum, and 7.6% came from extracellular exosomes, hemoglobin complex, immune complex, golgi apparatus, mitochondria, and peroxisome. Only 9.1% of the total antigens identified were of unknown location.

Discussion

The present work provides important information characterizing the antigenicity of BP for the use of xenogeneic biomaterials, while establishing and validating a novel affinity chromatography approach for antigen identification. Critically, unlike previously published 2-DE Western blot procedures, we demonstrate that the developed affinity chromatography approach achieves: (1) high-throughput identification of antigenic proteins, (2) compatibility with a wide range of protein solubility's, most importantly allowing for identification of integral membrane antigens and, (3) increased sensitivity compared to 2-DE immunoproteomic methods. Importantly, we further demonstrate that antigenic components of a commonly utilized xenogeneic biomaterial, BP, are associated with all tissue compartments. These findings carry important implications for the development of unfixed xenogeneic extracellular matrix (ECM) scaffolds as potentially ideal biomaterials for heart valve tissue engineering and regenerative medicine applications (17). Critically, the finding of non-cellular antigens brings into question the use of tissue acellularity as the primary outcome measure in decellularization approaches (18). Consequently, the presented findings have application toward the understanding of graft-specific immune responses to xenogeneic biomaterials, for monitoring of such responses in individual patients and for development of new xenogeneic ECM scaffolds in heart valve bioprostheses.

Previously utilized methods for assessment of xenogeneic biomaterial antigenicity have achieved limited success due to their challenging reproducibility and inability to resolve highly lipophilic proteins (12). Reproducibility of 2-DE approaches and poor specificity of identifications has commonly plagued this technique (19,20). In particular, issues such as multiple proteins in a single spot are especially problematic in antigen identification where high specificity is critical (21). Additionally, highly lipophilic proteins are poorly represented using 2-DE approaches due to their challenging solubility profile particularly during IEF focusing (14). For example, Beleoken et al. found twelve hepatic autoantigens associated with graft versus host disease, however, no integral membrane antigens were identified (22). Similarly, Biswas et al., identified 18 rheumatoid arthritis autoantigens, none of which were integral membrane antigens (23). Even when utilizing an additional membrane enriching step during protein isolation, Byrne et al. found only a single integral membrane antigen out of their 38 putative antigens in a pig-to-primate cardiac transplant model (24). In previously reported studies of BP, only 9.6% of 31 identified xenoantigens were non-cellular in origin and none were integral membrane antigens (13). Compared to previously reported 2-DE immunoproteomic methods, the developed affinity chromatography approach was able to identify 18 integral membrane antigens (13.5% of all antigens identified), almost all of which were found in the NDSB-L extract (FIG. 7), even though it had the lowest protein yield (FIG. 3). Given the difficulty of separating integral membrane proteins on a 2-DE format (12), not to mention the requirement of additional de-lipidation steps (13), the affinity chromatography approach utilized here provides an important advance in the field of protein antigen identification. Furthermore, the affinity chromatography approach successfully identified ten BP xenoantigens which had been identified using the previously reported 2-DE immunoproteomic method, including alpha-1-acid glycoprotein, apoplipoprotein A-1, annexin A5, alpha-1B glycoprotein, albumin, beta hemoglobin, hemopexin, superoxide dismutase, mimecan, also known as osteoglycin, and thy-1 (13). It is not surprising that the developed affinity chromatography approach did not identify all of the antigens previously identified using 2-DE immunoproteomic methods, as no proteomic approach is capable of resolving the entire proteome (13,25). Excitingly however, more than 100 additional previously unreported BP antigens were identified in this single experiment, indicating greater sensitivity than previous 2-DE methods (13). The pre-fractionation process was validated by the fact that the majority of the antigens discovered corresponded to their expected subcellular locations. The NDSB-H fraction contained predominantly soluble secreted antigens, while NDSB-L extracts contained the greatest number of cell membrane associated antigens. Finally, beyond simply overcoming previous immunoproteomic pitfalls, this approach only requires 5-8 hours to run, and has been successfully multiplexed to run up to 28 samples in a single experiment. Therefore, the affinity chromatography antigen identification approach overcomes the limitations of previously published immunoproteomic methods, facilitating rapid, high-throughput identification of both hydrophilic and highly lipophilic (i.e., integral membrane) antigens.

Across antigen identification studies, regardless of disease entity or species under investigation, a relatively small number of antigens are consistently identified, which commonly include isoforms of proteins from the same family (13,26). These findings suggest the possibility that shared epitope domains may exist among protein family members. This has been proposed (13) and validated by other researchers (26,27), with one group using epitopes to predict whole antigenic protein families (28). Indeed, in the present study, since animal models are expected to generate a robust immune response, it is intriguing that a relatively small subset of proteins within BP was identified as antigenic. Furthermore, 31 of the antigens identified in the current study have also been implicated as antigens in the pathogenesis of human diseases (29-34) the majority of them through identification of their antigen specific antibodies (22-24,35-48). A Basic Local Alignment Search Tool (BLAST) search between rabbit and bovine for these previously identified antigens showed them to share between 40-99% homology (49), with 11 of the antigens sharing greater than 93% homology. This high level of species homology suggests that rather than xenogeneic in-homology determining antigenicity, it is possible that context in which the immune system encounters the antigen is responsible for stimulating the adaptive immune response for many of the identified antigens. Finally, many of the discovered antigens were isoforms of each other such as Annexin A1, A2, and 4; Apolipoprotein A-1, A-11, and C-111; several subunits of ATP synthase; the gamma-12, beta-1 and beta-2 subunits of Guanine nucleotide-binding protein; and Serpin A3-2, Serpin H1 and SERPIND1, which are a part of the Serpin superfamily (50). Given that so many of the antigens were from the same protein families, a conserved epitope domain could help explain this phenomenon and may represent an interesting target for further investigations. By expanding the number and spectrum of identified antigens, affinity chromatography immunoproteomic methods have the potential to facilitate comparison between antigenic proteins and further fundamental understanding of immune system antigen recognition.

Due to the large number of proteins identified in the current report, a deeper insight into the critical biologic processes associated with graft-specific responses could be gained. Three processes were of particular interest: the immune response, coagulation, and inflammation accounted for 10.5%, 6%, and 3.8% of total antigen identifications. Compare this to the percentage of proteins associated with those processes in the total Bovine UniProt proteome at 4.3%, 0.2%, and 1.5% respectively (16), it is clear that these processes are overrepresented as antigenic. Furthermore, these processes are not only intertwined but are also involved with the success or failure of biomaterials (51) and polymorphisms within these systems have been implicated in other disease states (52,53). For example, previous investigations have implicated MEW class I polypeptide-related sequence A (MICA), as an immune-related non-human leukocyte antigen (non-HLA).54 Future efforts to identify non-HLA antigens may therefore benefit by focusing on immune response, coagulation and inflammation related biological processes. Other processes that were enriched were cell adhesion (6.8% of identifications) and ion transport (5.3% of identifications), compared to UniProt proteome abundance of 1.3% and 0.3% respectively. The importance of these biological processes is currently unknown and therefore warrants future investigation. The finding that specific biologic pathways are overrepresented in antigenic targets has potential to further our understanding of what makes a protein antigenic, which could be vastly beneficial for the field of tissue engineering and control of graft-specific immune responses as a whole.

Currently antigenicity is the major barrier for the use of animal derived tissues in biomaterials. A significant amount of effort has been put into generating screening assays and monitoring tools using galactose-β-1,3-galactose (β-gal) (55) and other known antigens (56). But it has been shown that β-gal is not the only source of xenoantigenicity (57) More success may be found by expanding our knowledge of antigenic tissue constituents. The approach presented here can be further applied to not only screen currently produced biomaterials, but to also educate their future production. Clearly, antigenic proteins are not only of cellular origin but can in fact be intimately associated with the matrix itself, furthering the evidence for a move away from "decellularized" tissues to "antigen-removed" tissues in biomaterial engineering (7,13). Increasing understanding of the xenoantigenic determinants of recipient graft-specific immune responses has important implications towards monitoring antibody titers in patients post-implantation, improving development of future xenogeneic biomaterials, and potentially even for development of tolerance induction strategies.

REFERENCES

1 Platt, J., DiSesa, V., Gail, D. & Massicot-Fisher, J. Recommendations of the National Heart, Lung, and Blood Institute Heart and Lung Xenotransplantation Working Group. Circulation 106, 1043-1047 (2002).
2 Manji, R. A., Lee, W. & Cooper, D. K. Xenograft bioprosthetic heart valves: Past, present and future. Int J Surg, doi:10.1016/j.ijsu.2015.07.009 (2015).
3 Zilla, P., Human, P. & Bezuidenhout, D. Bioprosthetic heart valves: the need for a quantum leap. Biotechnol Appl Bioc 40, 57-66, doi:10.1042/Ba20030211 (2004).
4 Simon, P. et al. Early failure of the tissue engineered porcine heart valve SYNERGRAFT in pediatric patients. Eur J Cardiothorac Surg 23, 1002-1006; discussion 1006 (2003).
5 Manji, R. A. et al. Glutaraldehyde-fixed bioprosthetic heart valve conduits calcify and fail from xenograft rejection. Circulation 114, 318-327, doi:10.1161/CIRCULATIONAHA.105.549311 (2006).
6 Badylak, S. F., Freytes, D. O. & Gilbert, T. W. Extracellular matrix as a biological scaffold material: Structure and function. Acta Biomater 5, 1-13, doi:10.1016/j.actbio.2008.09.013 (2009).
7 Wong, M. L. & Griffiths, L. G. Immunogenicity in xenogeneic scaffold generation: antigen removal vs. decellularization. Acta Biomater 10, 1806-1816, doi: 10.1016/j.actbio.2014.01.028 (2014).
8 Meyer, S. R. et al. Comparison of aortic valve allograft decellularization techniques in the rat. J Biomed Mater Res A 79, 254-262, doi:10.1002/jbm.a.30777 (2006).
9 Kasimir, M. T. et al. Decellularization does not eliminate thrombogenicity and inflammatory stimulation in tissue-engineered porcine heart valves. J Heart Valve Dis 15, 278-286; discussion 286 (2006).
10 Goncalves, A. C., Griffiths, L. G., Anthony, R. V. & Orton, E. C. Decellularization of bovine pericardium for tissue-engineering by targeted removal of xenoantigens. J Heart Valve Dis 14, 212-217 (2005).
11 Wheeler, C. H. et al. Characterization of endothelial antigens associated with transplant-associated coronary artery disease. J Heart Lung Transplant 14, S188-197 (1995).
12 Rabilloud, T. Membrane proteins and proteomics: love is possible, but so difficult. Electrophoresis 30 Suppl 1, S174-180, doi:10.1002/elps.200900050 (2009).
13 Griffiths, L. G., Choe, L. H., Reardon, K. F., Dow, S. W. & Christopher Orton, E. Immunoproteomic identification of bovine pericardium xenoantigens. Biomaterials 29, 3514-3520, doi:10.1016/j.biomaterials.2008.05.006 (2008).
14 Li, Z. B., Flint, P. W. & Boluyt, M. O. Evaluation of several two-dimensional gel electrophoresis techniques in cardiac proteomics. Electrophoresis 26, 3572-3585, doi: 10.1002/elps.200500104 (2005).
15. Baker, E. S. et al. Mass spectrometry for translational proteomics: progress and clinical implications. Genome Med 4, 63, doi:10.1186/gm364 (2012).
16. UniProt, C. UniProt: a hub for protein information. Nucleic Acids Res 43, D204-212, doi:10.1093/nar/gku989 (2015).
17. Dong, X. C. et al. RGD-modified acellular bovine pericardium as a bioprosthetic scaffold for tissue engineering. J Mater Sci-Mater M 20, 2327-2336, doi: 10.1007/s10856-009-3791-4 (2009).
18. Wong, M. L. & Griffiths, L. G. Immunogenicity in xenogeneic scaffold generation: Antigen removal vs. decellularization. Acta Biomater 10, 1806-1816, doi: 10.1016/j.actbio.2014.01.028 (2014).
19. Magdeldin, S. et al. Basics and recent advances of two dimensional-polyacrylamide gel electrophoresis. Clin Proteom 11, doi:Artn 1610.1186/1559-0275-11-16 (2014).
20. Posch, A. et al. 2D-ToGo workflow: increasing feasibility and reproducibility of 2-dimensional gel electrophoresis. Arch Physiol Biochem 119, 108-113, doi:10.3109/13813455.2013.791699 (2013).
21. Campostrini, N. et al. Spot overlapping in two-dimensional maps: A serious problem ignored for much too long. Proteomics 5, 2385-2395, doi:10.1002/pmic.200401253 (2005).
22. Beleoken, E. et al. Immunoproteomic analysis of potentially severe non-graft-versus-host disease hepatitis after allogenic bone marrow transplantation. Hepatology 57, 689-699, doi:10.1002/hep.26024 (2013).
23. Biswas, S. et al. Identification of Novel Autoantigen in the Synovial Fluid of Rheumatoid Arthritis Patients Using an Immunoproteomics Approach. Plos One 8, doi:ARTN e5624610.1371/journal.pone.0056246 (2013).
24. Byrne, G. W. et al. Proteomic identification of non-Gal antibody targets after pig-to-primate cardiac xenotransplantation. Xenotransplantation 15, 268-276, doi:10.1111/j.1399-3089.2008.00480.x (2008).
25. Essader, A. S., Cargile, B. J., Bundy, J. L. & Stephenson, J. L. A comparison of immobilized pH gradient isoelectric focusing and strong-cation-exchange chromatography as a first dimension in shotgun proteomics. Proteomics 5, 24-34, doi:DOI 10.1002/pmic.200400888 (2005).
26. Liu, Y. et al. Conserved epitopes in the protein tyrosine phosphatase family of diabetes autoantigens. Ann N Y Acad Sci 1150, 245-247, doi:10.1196/annals.1447.035 (2008).
27. Jimenez-Lopez, J. C., Gachomo, E. W., Ariyo, O. A., Baba-Moussa, L. & Kotchoni, S. O. Specific conformational epitope features of pathogenesis-related proteins mediating cross-reactivity between pollen and food allergens. Mol Biol Rep 39, 123-130, doi:10.1007/s11033-011-0717-2 (2012).
28. Kozlova, E. E. G., Viart, B. T., de Avila, R. A. M., Felicori, L. F. & Chavez-Olortegui, C. Classification epitopes in groups based on their protein family. BMC bioinformatics 16, doi:Artn S710.1186/1471-2105-16-S19-S7 (2015).
29. Okroj, M., Heinegard, D., Holmdahl, R. & Blom, A. M. Rheumatoid arthritis and the complement system. Ann Med 39, 517-530, doi:10.1080/07853890701477546 (2007).
30. Zhao, X. et al. Circulating immune complexes contain citrullinated fibrinogen in rheumatoid arthritis. Arthritis Res Ther 10, R94, doi:10.1186/ar2478 (2008).
31. Martinez-Flores, J. A. et al. Detection of circulating immune complexes of human IgA and beta 2 glycoprotein I in patients with antiphospholipid syndrome symptomatology. J Immunol Methods 422, 51-58, doi:10.1016/j.jim.2015.04.002 (2015).
32. Kruger, R. et al. Extracellular matrix biomarker, fibulin-1, is closely related to NT-proBNP and soluble urokinase plasminogen activator receptor in patients with aortic valve stenosis (the SEAS study). Plos One 9, e101522, doi:10.1371/journal.pone.0101522 (2014).
33. Martin-Rojas, T. et al. iTRAQ proteomic analysis of extracellular matrix remodeling in aortic valve disease. Sci Rep-Uk 5, doi:ARTN 1729010.1038/5rep17290 (2015).
34. Gu, G. R. et al. Lumican as a novel potential clinical indicator for acute aortic dissection: A comparative study, based on multi-slice computed tomography angiography. Exp Ther Med 11, 923-928, doi:10.3892/etm.2016.3020 (2016).
35. Kulik, L. et al. Pathogenic natural antibodies recognizing annexin IV are required to develop intestinal ischemia-reperfusion injury. J Immunol 182, 5363-5373, doi: 10.4049/jimmunol.0803980 (2009).
36. Meyers, L. et al. A role for Apolipoprotein A-I in the pathogenesis of multiple sclerosis. J Neuroimmunol 277, 176-185, doi:10.1016/j.jneuroim.2014.10.010 (2014).
37. Canas, F., Simonin, L., Couturaud, F. & Renaudineau, Y. Annexin A2 autoantibodies in thrombosis and autoimmune diseases. Thromb Res 135, 226-230, doi:10.1016/j.thromres.2014.11.034 (2015).
38. Schulze, K., Becker, B. F. & Schultheiss, H. P. Antibodies to the ADP/ATP carrier, an autoantigen in myocarditis and dilated cardiomyopathy, penetrate into myocardial cells and disturb energy metabolism in vivo. Circ Res 64, 179-192 (1989).
39. Caster, D. J. et al. Autoantibodies targeting glomerular annexin A2 identify patients with proliferative lupus nephritis. Proteomics Clin Appl 9, 1012-1020, doi: 10.1002/prca.201400175 (2015).
40. Alard, J. E. et al. Autoantibodies to endothelial cell surface ATP synthase, the endogenous receptor for hsp60, might play a pathogenic role in vasculatides. Plos One 6, e14654, doi:10.1371/journal.pone.0014654 (2011).
41. Mustafa, M. Z. et al. Autoantibody signatures defined by serological proteome analysis in sera from patients with cholangiocarcinoma. J Transl Med 14, 17, doi:10.1186/s12967-015-0751-2 (2016).
42. Skoldberg, F. et al. Identification of AHNAK as a novel autoantigen in systemic lupus erythematosus. Biochem Bioph Res Co 291, 951-958, doi:10.1006/bbrc.2002.6534 (2002).
43. Regent, A. et al. Identification of Target Antigens of Anti-Endothelial-Cell and Anti-Vascular-Smooth-Muscle-Cell Antibodies in Patients with Giant Cell Arteritis: A Proteomic Approach. Inflamm Res 60, 182-183 (2011).
44. Kimura, A. et al. Identification of target antigens of naturally occurring autoantibodies in cerebrospinal fluid. J Proteomics 128, 450-457, doi:10.1016/j.jprot.2015.05.005 (2015).
45. Zhang, Q. H. & Reed, E. F. Non-MHC antigenic targets of the humoral immune response in transplantation. Curr Opin Immunol 22, 682-688, doi:10.1016/j.coi.2010.08.009 (2010).

46 Dervan, E. W. et al. Protein Macroarray Profiling of Serum Autoantibodies in Pseudoexfoliation Glaucoma. Invest Ophth Vis Sci 51, 2968-2975, doi:10.1167/iovs.09-4898 (2010).

47 Borozdenkova, S. et al. Use of proteomics to discover novel markers of cardiac allograft rejection. J Proteome Res 3, 282-288, doi:10.1021/pr034059r (2004).

48 Miyaji, K., Paul, F., Shahrizaila, N., Umapathi, T. & Yuki, N. Autoantibodies to tetraspanins (CD9, CD81 and CD82) in demyelinating diseases. Journal of Neuroimmunology 291, 78-81, doi:10.1016/j.jneuroim.2015.12.012 (2016).

49 McGinnis, S. & Madden, T. L. BLAST: at the core of a powerful and diverse set of sequence analysis tools. Nucleic Acids Res 32, W20-W25, doi:10.1093/nar/gkh435 (2004).

50 Silverman, G. A. et al. The serpins are an expanding superfamily of structurally similar but functionally diverse proteins—Evolution, mechanism of inhibition, novel functions, and a revised nomenclature. J Biol Chem 276, 33293-33296, doi:DOI 10.1074/jbc.R100016200 (2001).

51 Zilla, P., Brink, J., Human, P. & Bezuidenhout, D. Prosthetic heart valves: catering for the few. Biomaterials 29, 385-406, doi:10.1016/j.biomaterials.2007.09.033 (2008).

52 Giles, J. L., Choy, E., van den Berg, C., Morgan, B. P. & Harris, C. L. Functional analysis of a complement polymorphism (rs17611) associated with rheumatoid arthritis. J Immunol 194, 3029-3034, doi:10.4049/jimmunol.1402956 (2015).

53 Adriani, K. S. et al. Common polymorphisms in the complement system and susceptiblity to bacterial meningitis. J Infect 66, 255-262, doi:10.1016/j.jinf.2012.10.008 (2013).

54 Dragun, D., Philippe, A. & Catar, R. Role of non-HLA antibodies in organ transplantation. Curr Opin Organ Transplant 17, 440-445, doi:10.1097/MOT.0b013e328355f12b (2012).

55 Naso, F. et al. First quantification of alpha-Gal epitope in current glutaraldehyde-fixed heart valve bioprostheses. Xenotransplantation 20, 252-261, doi:10.1111/xen.12044 (2013).

56 Anglicheau, D., Naesens, M., Essig, M., Gwinner, W. & Marquet, P. Establishing Biomarkers in Transplant Medicine: A Critical Review of Current Approaches. Transplantation 100, 2024-2038, doi:10.1097/TP.0000000000001321 (2016).

57 Griesemer, A., Yamada, K. & Sykes, M. Xenotransplantation: immunological hurdles and progress toward tolerance. Immunol Rev 258, 241-258, doi:10.1111/imr.12152 (2014).

58 Wong, M. L., Wong, J. L., Athanasiou, K. A. & Griffiths, L. G. Stepwise solubilization-based antigen removal for xenogeneic scaffold generation in tissue engineering. Acta Biomater 9, 6492-6501, doi:10.1016/j.actbio.2012.12.034 (2013).

59 Institute of Laboratory Animal Resources (U.S.). Committee on Care and Use of Laboratory Animals. in NIH publication v. (U.S. Dept. of Health and Human Services, Public Health Service, Bethesda, Md.).

60 Ma, Z. Q. et al. IDPicker 2.0: Improved protein assembly with high discrimination peptide identification filtering. Journal of proteome research 8, 3872-3881, doi:10.1021/pr900360j (2009).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for rapid screening and identification of eluted hydrophilic and/or lipophilic antigenic components present in a tissue or whole organ from a subject exposed to the tissue or whole organ, comprising the steps of:
   (a) obtaining a first biological sample comprising blood from the subject who has been exposed to antigenic components of the tissue or whole organ; and obtaining a second biological sample comprising the tissue or whole organ from the subject;
   (b) attaching immunoglobulins, or fragments thereof, isolated from the first biological sample to a column, thereby creating an affinity chromatography column comprising the immobilized immunoglobulins, or fragments thereof;
   (c) extracting hydrophilic and lipophilic antigenic components from a second biological sample by a two-step extraction process comprising, sequentially exposing the second biological sample to:
      (i) a hydrophilic solubilization solution selected from the group consisting of 3-(Benzyl-dimethylammonio)propanesulfonate (NDSB-256); 3-[N,N-Dimethyl(3-myristoylaminopropyl)amino]-propanesulfonate (ASB-14); 3[N,N-Dimethyl-(3-palmitoylaminopropyl)ammonio]-propanesulfonate (ASB-16); 4-n-Octylbenzoylamido-propyl-dimethylammoniosulfobetaine (ASB-C80); 3-(N,N-Dimethyloctylammonio)-propanesulfonate inner salt (SB3-8); N-Decyl-N,N-dimethyl-3-ammonio-1-propanesulfonate (SB3-10); N-Tetradecyl-N,N-dimethyl-3-ammonio-1-propanesulfonate (SB3-14); 3-(N,N Dimethylpalmitylammonio)propanesulfonate (SB3-16); and 3-(N,N-Dimethyloctadecylammonio)propanesulfonate (SB3-18); and
      (ii) a lipophilic solubilization solution selected from the group consisting of 3-(Benzyldimethyl-ammonio)propanesulfonate (NDSB-256) and 1% (w/v) n-dodecyl-β-D-maltoside (NDSB-L); 3-[N,N-Dimethyl(3-myristoylaminopropyl)amino]propanesulfonate (ASB-14); 3-[N,N-Dimethyl-(3-palmitoyl-aminopropyl)ammonio]propanesulfonate (ASB-16); 4-n-Octylbenzoylamido-propyl-dimethylammoniosulfobetaine (ASB-C80); 3-(N,N-Dimethyloctylammonio)propanesulfonate inner salt (SB3-8); N-Decyl-N,N-dimethyl-3-ammonio-1-propane-sulfonate (SB3-10); N-Tetradecyl-N,N-dimethyl-3-ammonio-1-propane-sulfonate (SB3-14); 3-(N,N Dimethylpalmitylammonio)-propanesulfonate (SB3-16); and 3-(N,N-Dimethyloctadecylammonio)propanesulfonate (SB3-18),
      wherein the lipophilic antigenic components are extracted by exposing the tissue or whole organ to a concentration of a lipophilic solubilization solution that is at least 5-fold greater than the concentration of the hydrophilic solubilization solution used to extract the hydrophilic antigenic components;
   (d) exposing the extracted hydrophilic and lipophilic antigenic components prepared from step (c) to the affinity chromatography column comprising the immobilized immunoglobulins, or fragments thereof from the first biological sample from steps (a) and (b), under conditions that allow antigenic components in the extracted hydrophilic and lipophilic antigenic components from step (c) to be bound or not be bound to the immunoglobulins, or fragments thereof on the affinity chromatography column;

(e) washing the affinity chromatography column to remove non-antigenic components that did not bind to the affinity chromatography column;

(f) eluting the bound antigenic components from the immobilized immunoglobulins, or fragments thereof on the affinity chromatography column, wherein eluting comprises exposing the bound antigenic components to a step-wise change or a gradient change in eluent properties selected from the group consisting of pH, salt concentration, acetonitrile concentration, and a combination thereof; and (g) identifying the eluted antigenic components prepared by step (f) by mass spectrometry, wherein the eluted antigenic components are selected from the group consisting of proteins, carbohydrates, and lipids.

2. The method of claim 1, wherein the tissue or whole organ is selected from the group consisting of a transplanted tissue and whole organ.

3. The method of claim 1, wherein the subject has been immunized with a sample of the tissue or the whole organ.

4. The method of claim 3, wherein the second biological sample of tissue or whole organ has been homogenized.

5. The method of claim 1, wherein the affinity chromatography column binds to the Fc portion of the immunoglobulins.

6. The method of claim 1, wherein the immunoglobulins are whole immunoglobulin molecules.

7. The method of claim 1, wherein the immunoglobulins are an immunoglobulin subclass selected from the group consisting of IgG, IgM, IgE, IgA, IgD, and mixtures thereof.

8. The method of claim 7, wherein the immunoglobulins comprise IgG subclass immunoglobulins selected from the group IgG1, IgG2, IgG3, IgG4, and mixtures thereof.

9. The method of claim 1, wherein the eluted antigenic components are identified by liquid chromatography-tandem mass spectrometry (LC-MS/MS).

10. The method of claim 1, wherein the method is multiplexed.

11. The method of claim 1, wherein the eluted antigenic components identified in step (g) comprise integral membrane antigens.

* * * * *